(12) United States Patent
Sundvor et al.

(10) Patent No.: US 12,031,979 B2
(45) Date of Patent: Jul. 9, 2024

(54) SYSTEM AND METHOD FOR DETECTION OF TARGET SUBSTANCES

(71) Applicant: Nima Acquisition, LLC, Northfield, IL (US)

(72) Inventors: Scott Sundvor, San Francisco, CA (US); Steven Portela, San Francisco, CA (US); Jonathan Ward, San Francisco, CA (US); John Walton, San Francisco, CA (US); Jonathan William Kiel, San Francisco, CA (US); Jeffrey Mekler, San Francisco, CA (US); Shireen Yates, San Francisco, CA (US); Jacob Mooney, San Francisco, CA (US); Dane Weitmann, San Francisco, CA (US); Joseph Horrell, San Francisco, CA (US)

(73) Assignee: Nima Acquisition, LLC, Northfield, IL (US)

( * ) Notice: Subject to any disclaimer, the term of this patent is extended or adjusted under 35 U.S.C. 154(b) by 333 days.

(21) Appl. No.: 16/704,184

(22) Filed: Dec. 5, 2019

(65) Prior Publication Data
US 2020/0110079 A1 Apr. 9, 2020

Related U.S. Application Data

(60) Continuation of application No. 16/278,388, filed on Feb. 18, 2019, now Pat. No. 10,533,995, which is a
(Continued)

(51) Int. Cl.
*G01N 33/53* (2006.01)
*B01L 3/00* (2006.01)
(Continued)

(52) U.S. Cl.
CPC ......... *G01N 33/5308* (2013.01); *G01N 33/02* (2013.01); *G01N 33/54366* (2013.01)

(58) Field of Classification Search
CPC .... G01N 33/5308; G01N 33/50; G01N 33/02; G01N 33/54366; G01N 15/06
See application file for complete search history.

(56) References Cited

U.S. PATENT DOCUMENTS

| 3,802,842 A | 4/1974 | Lange et al. |
| 4,066,511 A | 1/1978 | Montagnon |

(Continued)

FOREIGN PATENT DOCUMENTS

| CN | 101166569 A | 4/2008 |
| CN | 101909757 A | 12/2010 |

(Continued)

OTHER PUBLICATIONS

Woodfolk et al., Allergens, sources, particles and molecules: Why do we make IgE response, Allergol. Int. 2015, 64(4), (25 pages) (Year: 2015).

(Continued)

*Primary Examiner* — Brian J. Sines
(74) *Attorney, Agent, or Firm* — Quarles & Brady LLP

(57) ABSTRACT

A system and method includes a test container for detecting a target substance in a consumable sample, where the test container includes a test container body defining a test container top, a test container bottom opposing the test container top, a first chamber proximal the test container top, and a second chamber proximal the test container bottom, a magnetic diaphragm situated between the first chamber and the second chamber, the magnetic diaphragm obstructing flow of the consumable sample, and the magnetic diaphragm including a magnetic element embedded in the magnetic diaphragm, and a driving element geometrically comple-
(Continued)

mentary to the first chamber, the driving element including a consumable sample grinding feature protruding from a surface of the driving element.

25 Claims, 18 Drawing Sheets

Related U.S. Application Data division of application No. 15/265,171, filed on Sep. 14, 2016, now Pat. No. 10,254,279, which is a continuation-in-part of application No. 14/498,298, filed on Sep. 26, 2014, now Pat. No. 9,939,432, which is a continuation-in-part of application No. 14/227,543, filed on Mar. 27, 2014, now Pat. No. 9,939,431.

(60) Provisional application No. 62/234,748, filed on Sep. 30, 2015, provisional application No. 62/218,196, filed on Sep. 14, 2015, provisional application No. 61/874,590, filed on Sep. 6, 2013, provisional application No. 61/806,425, filed on Mar. 29, 2013.

(51) Int. Cl.
  G01N 33/02 (2006.01)
  G01N 33/543 (2006.01)

(56) References Cited

U.S. PATENT DOCUMENTS

| | | | |
|---|---|---|---|
| 4,250,256 | A | 2/1981 | Bleisteiner et al. |
| 4,822,174 | A | 4/1989 | Deibel |
| 4,960,691 | A | 10/1990 | Gordon |
| 5,143,084 | A | 9/1992 | Macemon et al. |
| 5,217,905 | A | 6/1993 | Marchand et al. |
| 5,256,372 | A | 10/1993 | Brooks et al. |
| 5,415,994 | A | 5/1995 | Imrich et al. |
| 5,504,013 | A | 4/1996 | Senior |
| 6,136,549 | A | 10/2000 | Feistel |
| 6,136,610 | A | 10/2000 | Polito et al. |
| 6,180,335 | B1 | 1/2001 | Wilkins et al. |
| 6,319,466 | B1 | 11/2001 | Markovsky et al. |
| 6,528,323 | B1 | 3/2003 | Thayer et al. |
| 6,616,893 | B1 | 9/2003 | Pham |
| 6,663,833 | B1* | 12/2003 | Stave .................. G01N 33/538 436/178 |
| 6,881,554 | B2 | 4/2005 | Dicesare et al. |
| 7,098,040 | B2 | 8/2006 | Kaylor et al. |
| 7,220,597 | B2 | 5/2007 | Zin et al. |
| 7,238,322 | B2 | 7/2007 | Wang et al. |
| 7,267,799 | B1 | 9/2007 | Borich et al. |
| 7,300,197 | B2 | 11/2007 | Mccurdy et al. |
| 7,371,582 | B2 | 5/2008 | Nahm et al. |
| 7,507,374 | B2 | 3/2009 | Gould et al. |
| 7,527,765 | B2 | 5/2009 | Royds |
| 7,560,272 | B2 | 7/2009 | Ramsey et al. |
| 7,585,529 | B2 | 9/2009 | Villar et al. |
| 7,749,771 | B2 | 7/2010 | Burgess-Cassler et al. |
| 7,776,266 | B2 | 8/2010 | Royds |
| 7,784,678 | B2 | 8/2010 | Kuo et al. |
| 7,932,099 | B2 | 4/2011 | Egan et al. |
| 7,972,871 | B2 | 7/2011 | Chandler |
| 7,995,196 | B1 | 8/2011 | Fraser |
| 8,211,715 | B1 | 7/2012 | Royds |
| 8,231,548 | B2 | 7/2012 | Hoenes |
| 8,278,091 | B2 | 10/2012 | Rutter et al. |
| 8,361,460 | B2 | 1/2013 | Morimatsu et al. |
| 8,632,730 | B2 | 1/2014 | Petrilla et al. |
| 9,005,551 | B2 | 4/2015 | Chen et al. |
| 9,201,068 | B2 | 12/2015 | Suni et al. |
| 9,285,331 | B2 | 3/2016 | Minteer et al. |
| 9,625,357 | B2 | 4/2017 | Bransky et al. |
| 10,533,995 | B2* | 1/2020 | Sundvor ............. G01N 33/5308 |
| 2003/0138819 | A1 | 7/2003 | Gong et al. |
| 2003/0138941 | A1 | 7/2003 | Gong et al. |
| 2003/0186458 | A1 | 10/2003 | Dicesare et al. |
| 2004/0018575 | A1 | 1/2004 | Rappin et al. |
| 2004/0022687 | A1 | 2/2004 | Wuske et al. |
| 2004/0132091 | A1 | 7/2004 | Ramsey et al. |
| 2004/0137137 | A1 | 7/2004 | Villar et al. |
| 2004/0141879 | A1 | 7/2004 | Loomis |
| 2004/0152209 | A1 | 8/2004 | Zin et al. |
| 2004/0189311 | A1 | 9/2004 | Glezer et al. |
| 2004/0265234 | A1 | 12/2004 | Morimatsu et al. |
| 2005/0112779 | A1 | 5/2005 | Wei et al. |
| 2005/0136553 | A1 | 6/2005 | Kaylor et al. |
| 2005/0147532 | A1 | 7/2005 | Bellet |
| 2005/0214866 | A1 | 9/2005 | McCall |
| 2005/0214951 | A1 | 9/2005 | Nahm et al. |
| 2005/0255533 | A1 | 11/2005 | Dantini et al. |
| 2006/0051237 | A1 | 3/2006 | Wang et al. |
| 2006/0204399 | A1 | 9/2006 | Freeman et al. |
| 2006/0240568 | A1 | 10/2006 | Petruno |
| 2006/0292035 | A1 | 12/2006 | Gould et al. |
| 2007/0041624 | A1 | 2/2007 | Cork |
| 2007/0047382 | A1 | 3/2007 | Mccurdy et al. |
| 2007/0054414 | A1 | 3/2007 | Burgess-Cassler et al. |
| 2007/0116595 | A1 | 5/2007 | Petrilla et al. |
| 2007/0238102 | A1* | 10/2007 | Song .................. C12Q 1/00 435/7.1 |
| 2007/0238138 | A1 | 10/2007 | Royds |
| 2007/0292899 | A1 | 12/2007 | Lovell |
| 2007/0292941 | A1 | 12/2007 | Handique et al. |
| 2008/0171397 | A1 | 7/2008 | Hardcastle et al. |
| 2008/0181821 | A1 | 7/2008 | Jung |
| 2008/0199851 | A1 | 8/2008 | Egan et al. |
| 2009/0047691 | A1 | 2/2009 | Huwig et al. |
| 2009/0136633 | A1 | 5/2009 | Royds |
| 2009/0148933 | A1 | 6/2009 | Battrell et al. |
| 2009/0154776 | A1 | 6/2009 | Mott |
| 2010/0129922 | A1 | 5/2010 | Gold et al. |
| 2010/0167309 | A1 | 7/2010 | Chandler |
| 2010/0210033 | A1 | 8/2010 | Scott |
| 2010/0222224 | A1 | 9/2010 | Suni et al. |
| 2010/0255609 | A1 | 10/2010 | Rutter et al. |
| 2010/0317033 | A1 | 12/2010 | Abdel |
| 2011/0039198 | A1 | 2/2011 | Ashley et al. |
| 2011/0044865 | A1 | 2/2011 | Groisman |
| 2011/0059550 | A1 | 3/2011 | Haik |
| 2011/0143968 | A1 | 6/2011 | Chen et al. |
| 2012/0046203 | A1 | 2/2012 | Walsh |
| 2012/0078455 | A1 | 3/2012 | Chrostowski et al. |
| 2012/0264232 | A1 | 10/2012 | Kramer et al. |
| 2013/0203043 | A1 | 8/2013 | Ozcan et al. |
| 2014/0033809 | A1* | 2/2014 | Bransky .............. G01N 1/2035 73/64.56 |
| 2014/0072960 | A1* | 3/2014 | Lansing ............. G01N 33/5302 435/7.1 |
| 2014/0120563 | A1 | 5/2014 | Ozcan et al. |
| 2014/0125835 | A1 | 5/2014 | Voss et al. |
| 2014/0174953 | A1 | 6/2014 | Elder |
| 2014/0186880 | A1 | 7/2014 | Lowenkamp |
| 2014/0227796 | A1 | 8/2014 | Gold et al. |
| 2014/0295406 | A1 | 10/2014 | Sundvor |
| 2014/0300696 | A1 | 10/2014 | Ozcan et al. |
| 2015/0011020 | A1 | 1/2015 | Sundvor |
| 2015/0072358 | A1* | 3/2015 | Luckert ............ G01N 33/56961 435/7.31 |
| 2015/0151300 | A1 | 6/2015 | Williams et al. |
| 2017/0003222 | A1 | 1/2017 | Neijzen et al. |
| 2019/0086430 | A1* | 3/2019 | Wang .................... G01N 33/82 |

FOREIGN PATENT DOCUMENTS

| | | |
|---|---|---|
| CN | 102629689 B | 5/2014 |
| CN | 102016574 B | 9/2014 |
| EP | 1034429 B1 | 11/2003 |
| EP | 1640718 A1 | 3/2006 |
| WO | 1999014595 A1 | 3/1999 |
| WO | 2005031351 A1 | 4/2005 |
| WO | 2006117129 A1 | 11/2006 |
| WO | 2011039198 A2 | 4/2011 |

(56) References Cited

FOREIGN PATENT DOCUMENTS

| WO | 2012078455 A1 | 6/2012 |
| WO | 2014047692 A1 | 4/2014 |
| WO | 2014176556 A1 | 10/2014 |
| WO | 2015017442 A2 | 2/2015 |

OTHER PUBLICATIONS

Wen et al. "A novel extraction method for peanut allergenic proteins in chocolate and their detection by a liposome-based lateral flow assay." Eur. Food Res. Technol. 22(1), (2005), p. 564-569. (Year: 2005).

Neogen Corporation, Food Allergen Handbook, Ninth Edition, Copyright 2012, 28 pages.

Extended European Search Report for EP Application No. 16762414.7 dated Oct. 11, 2018.

Office Action for Chinese Patent Application No. 201680014283.2 dated Apr. 3, 2019.

* cited by examiner

Elevation Schmatic

Isometric View

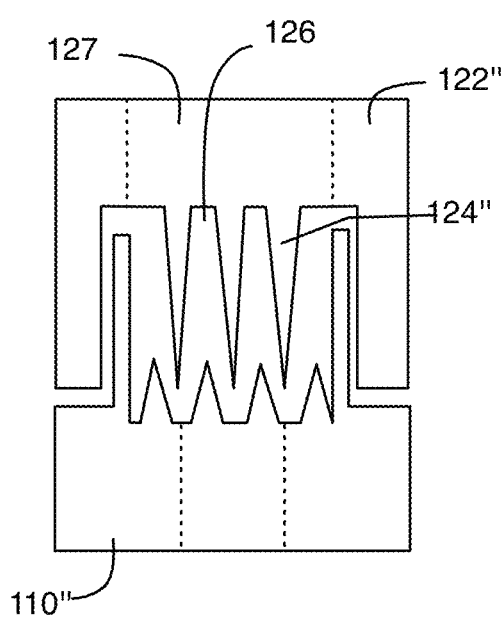
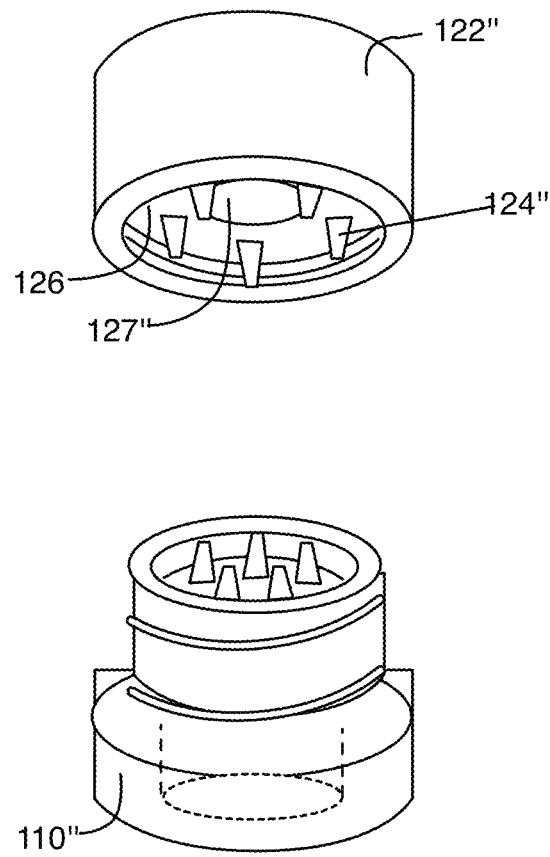
Elevation Schmatic
FIGURE 4A
Isometric View
FIGURE 4B

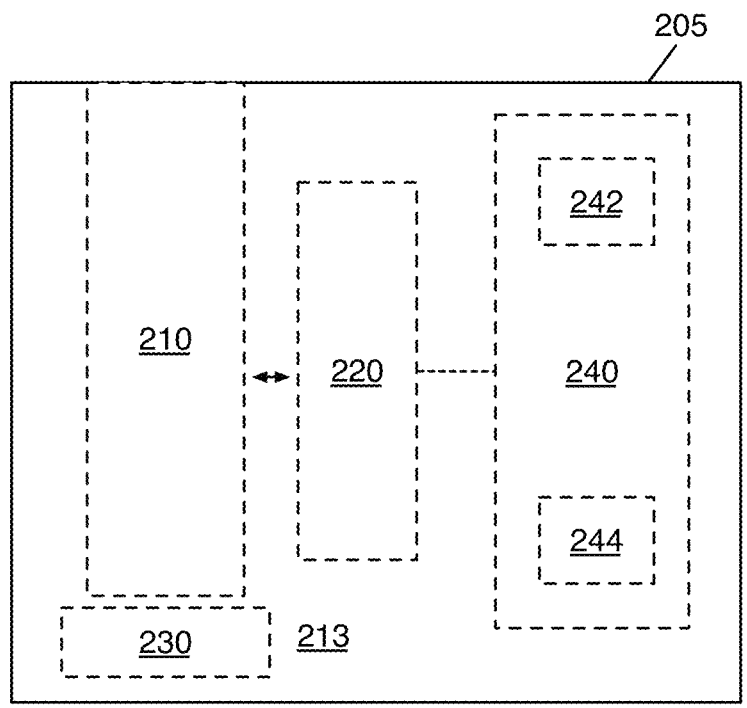
FIGURE 9A
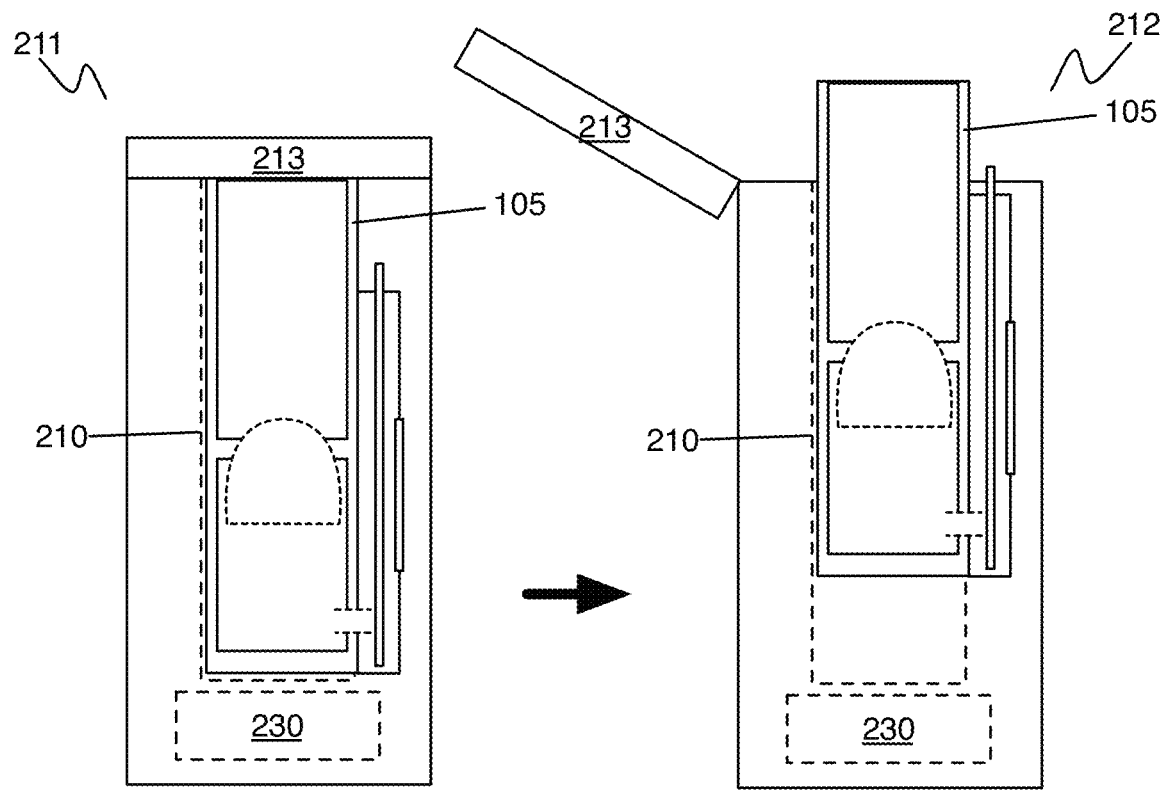
FIGURE 9B
FIGURE 9C

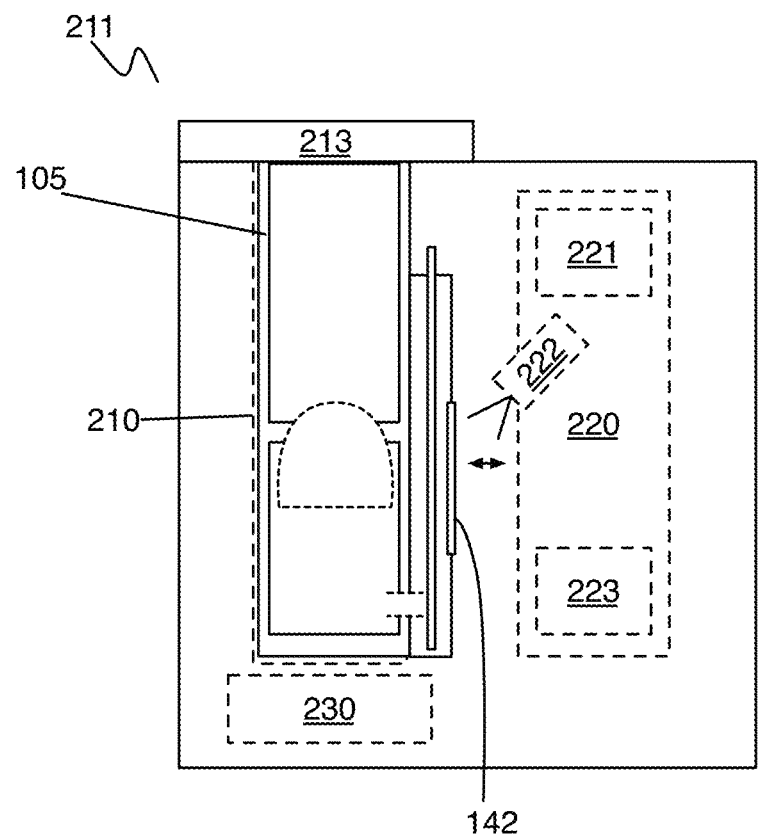
FIGURE 10
Pre-processing Image of 150
Post-processing Image of 150
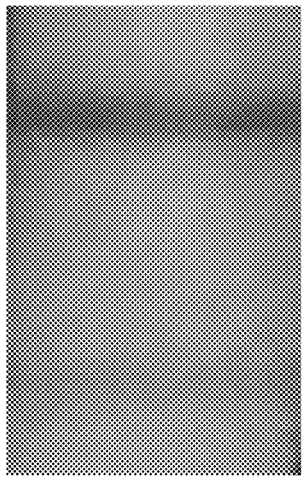
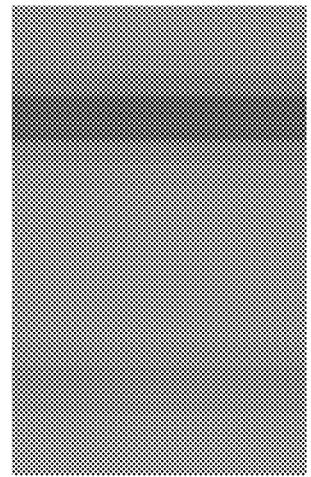
FIGURE 11A  FIGURE 11B

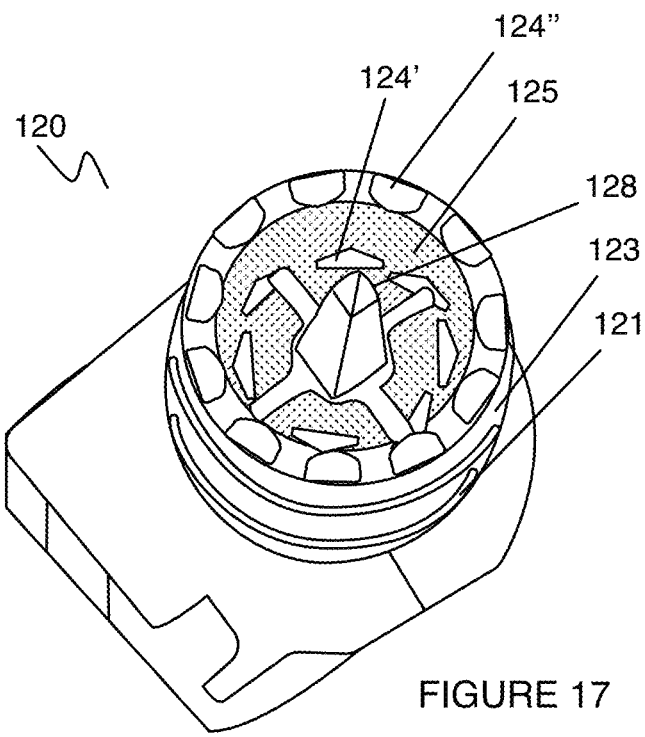
FIGURE 17
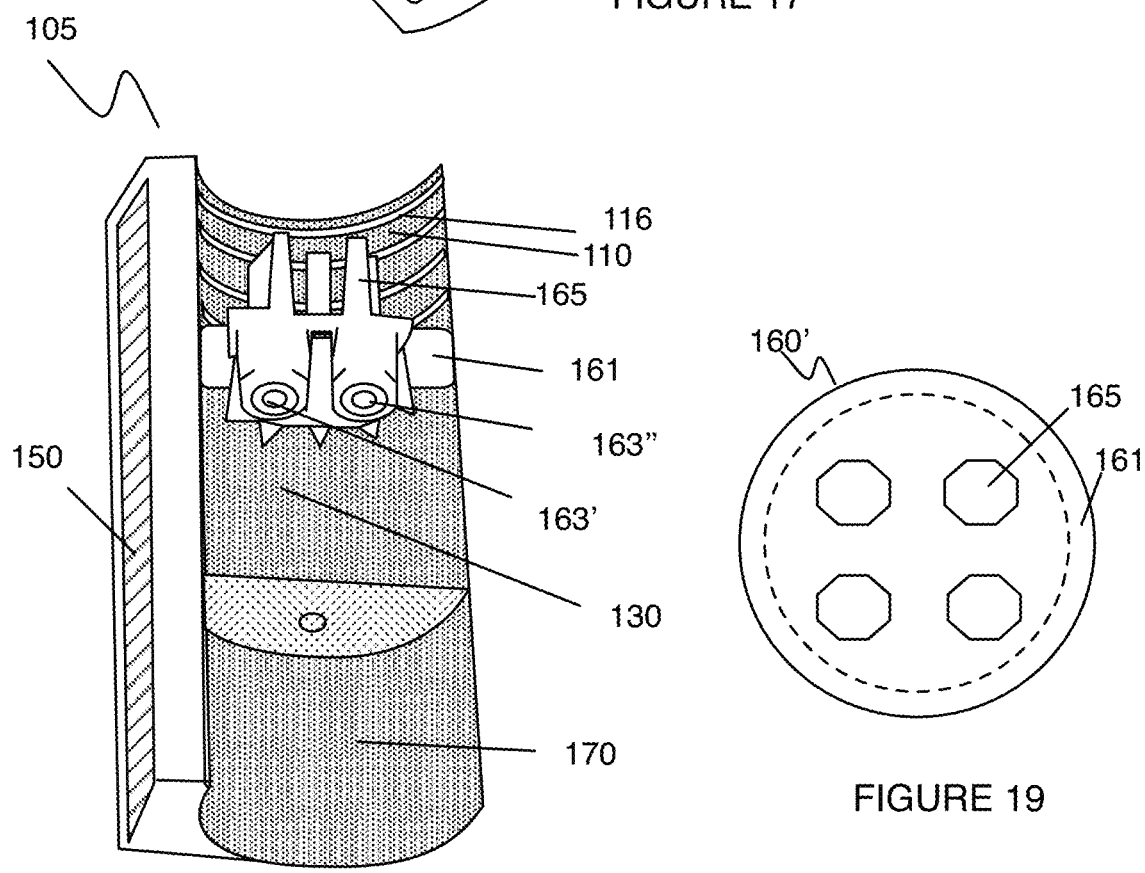
FIGURE 18
FIGURE 19

SYSTEM AND METHOD FOR DETECTION OF TARGET SUBSTANCES

CROSS-REFERENCE TO RELATED APPLICATIONS

This application is a continuation of U.S. Ser. No. 16/278,388 filed 18 Feb. 2019, which is a divisional application of U.S. application Ser. No. 15/265,171 filed 14 Sep. 2016, which is a Continuation-In-Part Application of U.S. application Ser. No. 14/498,298, filed 26 Sep. 2014, which is a Continuation-in-Part Application of U.S. application Ser. No. 14/227,543, filed on 27 Mar. 2014, which claims the benefit of U.S. Provisional Application Ser. No. 61/874,590, filed on 6 Sep. 2013, and U.S. Provisional Application Ser. No. 61/806,425, filed on 29 Mar. 2013, all of which are each incorporated herein in their entirety by this reference.

This application is a continuation of U.S. Ser. No. 16/278,388 filed 18 Feb. 2019, which is a divisional application of U.S. application Ser. No. 15/265,171 filed 14 Sep. 2016 which claims priority to U.S. Provisional No. 62/218,196 filed 14 Sep. 2015 and U.S. Provisional Application No. 62/234,748 filed 30 Sep. 2015, which are each incorporated in their entireties by this reference.

TECHNICAL FIELD

This invention relates generally to the consumer assay device field, and more specifically to an improved system and method for detection of target substances within a consumable.

BACKGROUND

A wide variety of consumables (e.g., foods, beverage, cosmetics, etc.) contain contaminants, toxins, allergens, and/or other substances that are of interest to all or specific types of consumers. In particular, in recent years, an increase in the number of consumers with an identified allergy (e.g., gluten allergy, dairy allergy, fish allergy, nut allergy, soy allergy, cosmetic allergy, etc.) has contributed to a number of products that omit ingredients having an associated allergen; however, such consumers are still at risk for consuming items with a harmful substance when the items do not have adequate labeling or documentation. Various systems and methods exist for detection of toxins and harmful substances present in a sample; however, current systems and methods are deficient due to one or more of: a time-intensive manner of receiving test results, a labor-intensive manner of receiving test results, a non-automated manner of processing samples, system bulk, system non-portability, and other factors that contribute to inconveniencing a consumer using such systems.

Due to these and other defects of current systems and methods for detecting harmful substances in consumables, there is thus a need for an improved system and method for detecting target substances. This invention provides such a system and method.

BRIEF DESCRIPTION OF THE FIGURES

FIGS. 4A and 4B depict second variations and examples of a portion of a system for detection of harmful substances;
FIGS. 9A-9E depict variations and configurations of a portion of a system for detection of harmful substances;
FIG. 10 depicts one variation of a portion of a system for detection of harmful substances;
FIGS. 11A and 11B depict example outputs of a system for detection of harmful substances;
FIG. 17 depicts a variation of a portion of a system for detection of harmful substances;
FIG. 18 depicts a variation of a test container of a system for detection of harmful substances;
FIG. 19 depicts a variation of a diaphragm of a system for detection of harmful substances.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1:
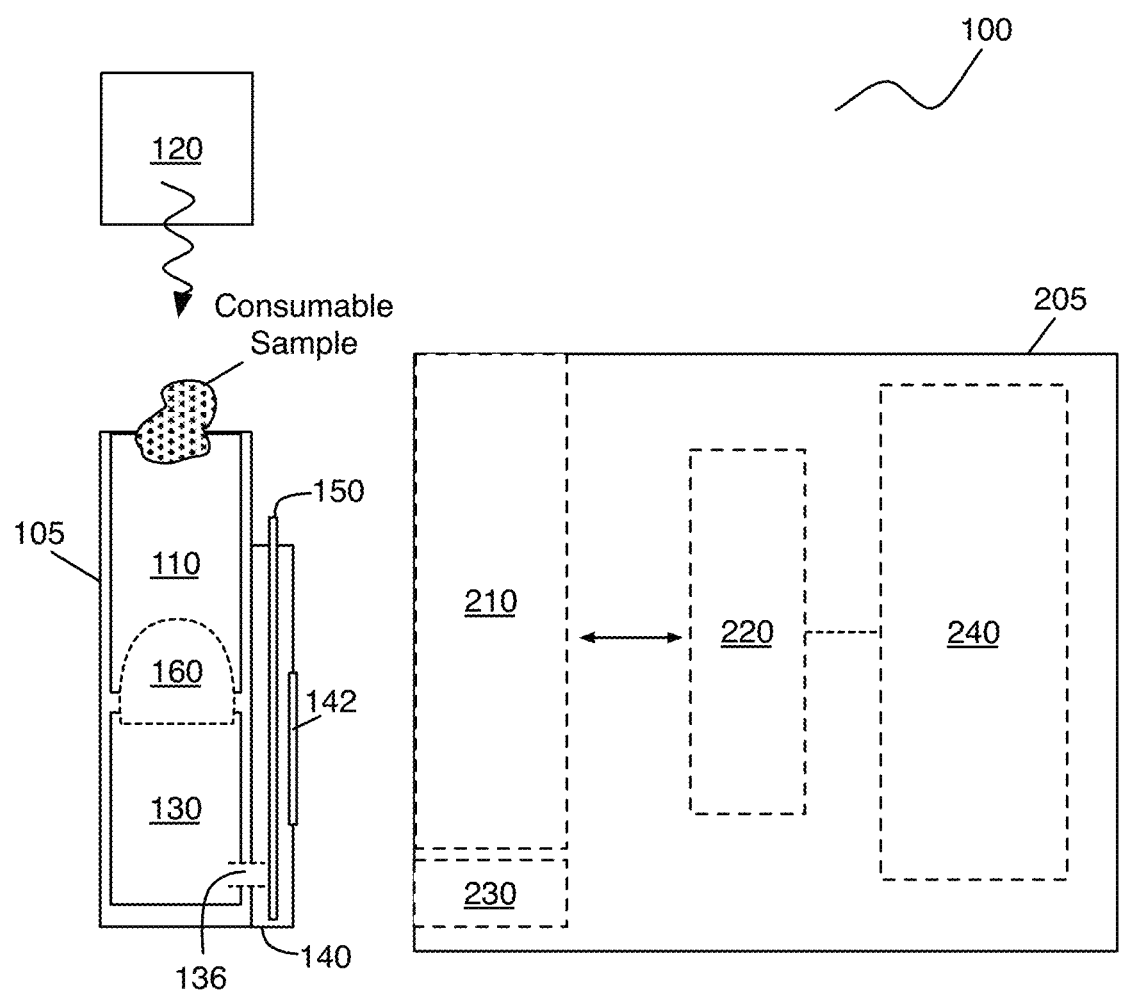
FIG. 1 depict an embodiment of a system for detection of harmful substances.
Figure 16A:
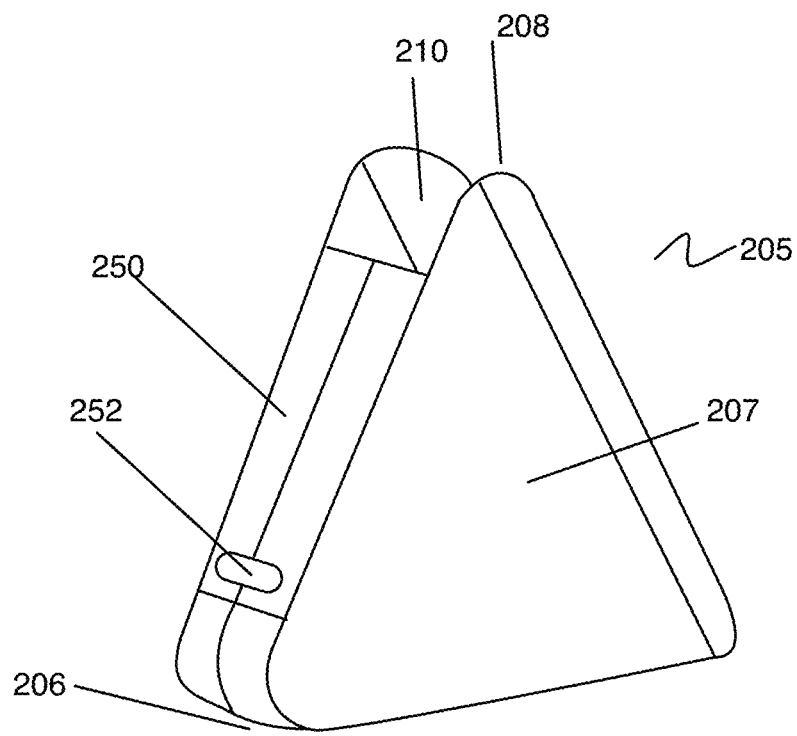
FIGS. 16A-16B depict schematics of an embodiment of a system for detection of harmful substances.
Figure 16B:
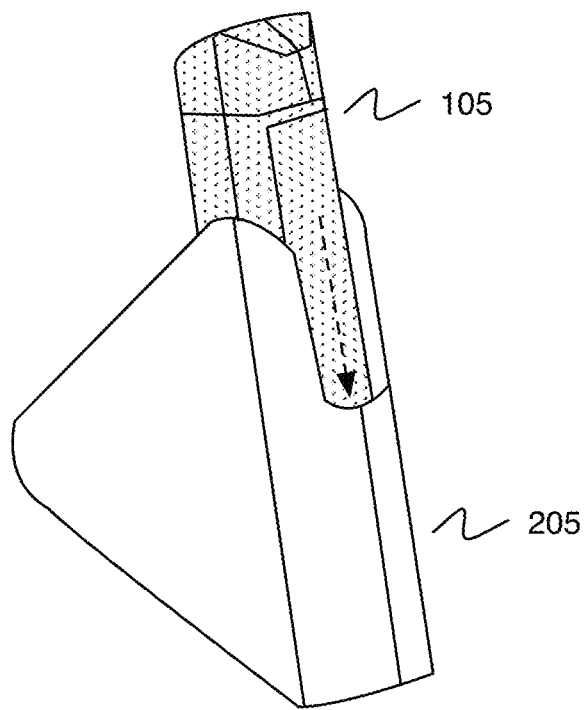

As shown in FIGS. 1 and 16B, an embodiment of a system 100 for detecting a target substance in a consumable sample includes: a test container 105 and an analysis device 205 configured to detect presence of the harmful substance at the test container 105. In an embodiment, the test container 105 includes: a first chamber 110 for receiving the consumable sample, a driving element 120 configured to generate a homogenized sample upon processing of the consumable sample, a second chamber 130 configured to receive the homogenized sample and combine it with a process reagent to produce a dispersion, and analysis chamber 140 configured to expose the dispersion to a detection substrate 150 for detection of the harmful substance. In an embodiment, the analysis device 205 includes: a receiving port 210 configured to receive the test container 105, an optical sensing subsystem 220 configured to enable detection of the presence of the harmful substance at the detection substrate 150, a mixing module 230 configured to mix the homogenized sample with a process reagent, and a processing and control system 240 configured to receive and process signals from the optical sensing subsystem 220, thereby producing an output indicative of the presence of the harmful substance in the consumable sample.

As shown in FIGS. 17-18, another embodiment of a system 100 includes a test container 105 for detecting a target substance in a consumable sample, where the test container 105 defines a first chamber 110, and a second chamber 130, a magnetic diaphragm 160' situated between the first chamber 110 and the second chamber 130, the magnetic diaphragm 160' obstructing flow of the consumable sample, the magnetic diaphragm 160' including one or more magnetic elements 163', 163" embedded in the magnetic diaphragm, and a driving element 120 geometrically complementary to the first chamber 110, the driving element including a consumable sample grinding feature extending from a surface of the driving element 120.

The system 100 functions to receive and process a sample of a consumable (e.g., food, beverage, cosmetic, etc.) in order to enable detection of one or more harmful substances within the sample. In examples, the harmful substances can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. The system 100 is preferably configured to impose minimal requirements upon a consumer using the system 100, in terms of labor-intensiveness, time-intensiveness, and cost-intensiveness. As such, the system 100 is preferably configured to automatically or semi-automatically process the sample in a manner that is intuitive to the consumer, and to quickly provide information regarding presence of the harmful substance(s) within the sample. The system 100 is preferably configured to be portable and compact, such that the user can conveniently carry the system 100 during his/her daily life (e.g., to establishments); however, in some alternative variations, the system 100 can be configured to be non-portable and/or non-compact. Preferably, the system 100 has reusable and disposable components, and in some variations portions of the system 100 are configured to be single-use (e.g., the test container(s), portions of a test container) while other portions of the system 100 are configured to be reusable (e.g., the analysis device). However, in other variations, the system 100 can include only reusable components or only disposable components.

In an example workflow, the system 100 is configured to receive a sample at a first chamber of a test container, to homogenize the sample, and to mix the homogenized sample with at least one process reagent to enable detection of one or more harmful substances within the sample at an analysis device. In the example workflow, a user of the system 100 would deposit the sample into the test container, perform a small amount of labor to facilitate homogenization of the sample, and place the container in the analysis device for further processing and analysis of the sample, such that the user has minimal interaction with the system 100 in generating an output. In another example workflow, the system 100 is configured to receive a sample at a first chamber of a test container, to homogenize the sample, and to mix the homogenized sample with at least one process reagent to enable detection of one or more harmful substances within the sample at an analysis device. In this example workflow, the system 100 is configured to receive and process a sample without any labor required by a user, in order to enable detection of a target substance within the sample in a fully-automated manner.

Figure 15:
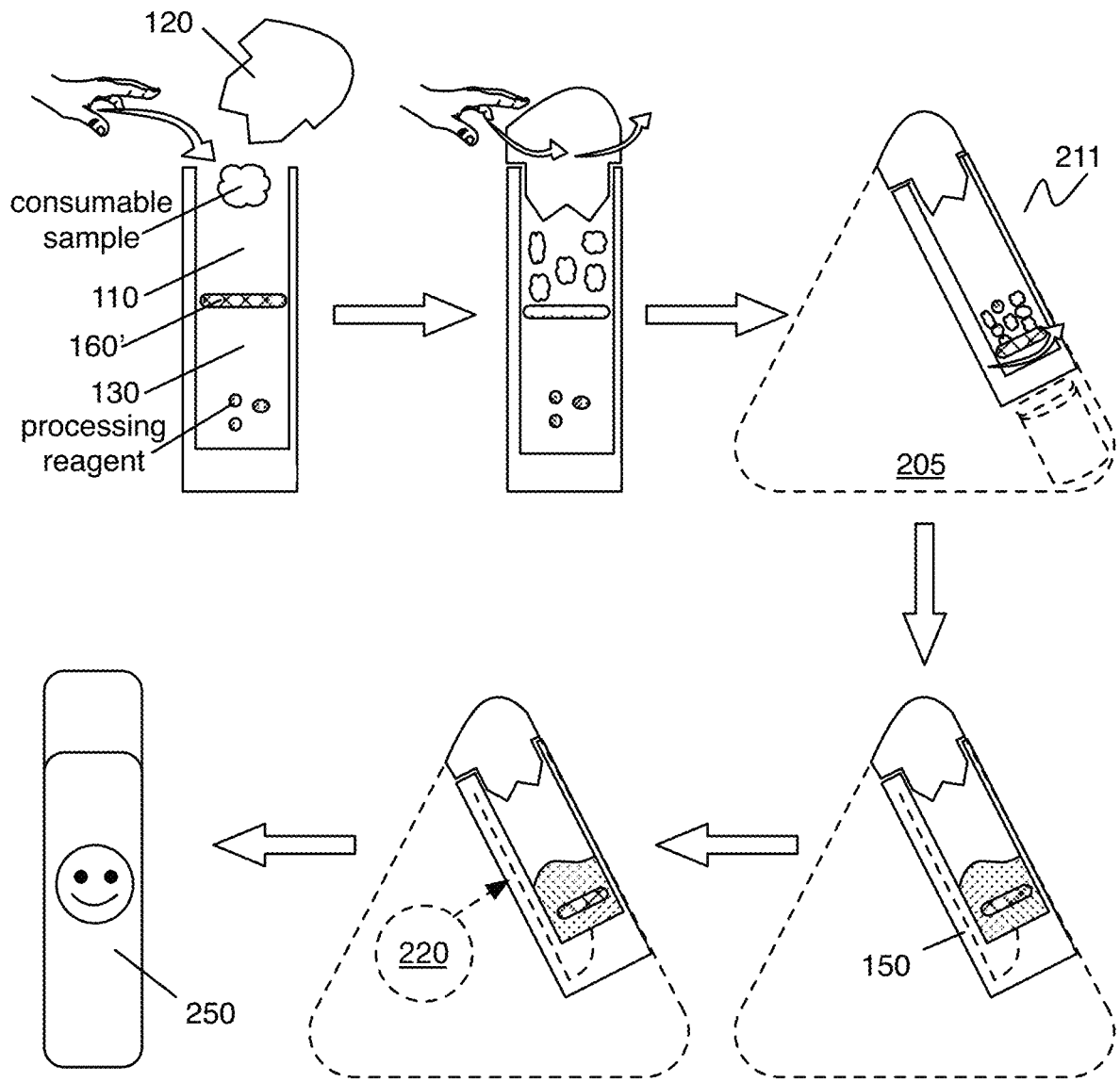
FIG. 15 depicts a schematic of an embodiment of a system for detection of harmful substances.

As shown in FIG. 15, in another example workflow, the system 100 can function to homogenize a food sample (e.g., with a test container cap 120 including grinding elements) within a grinding chamber 110 of a disposable test container 105 as a user rotates the cap to seal the test container 105. The system 100 can additionally function to mix the homogenized sample (e.g., where the system 100 is configured to magnetically rotate a detachable diaphragm that falls into the mixing chamber 130 after detachment of the diaphragm from the test container walls) with the appropriate processing reagents, to flow the consumable sample to a beginning portion of a detection substrate 150 (e.g., test strip), to perform an optical analysis with an optical sensing subsystem 220 of a complementary analysis device 205, and to display results on a user interface 250 (e.g., an indicator of whether or not allergens were detected).

As such, the system is preferably configured to facilitate implementation of the method 300 described in Section 2 below; however, the system 100 can additionally or alternatively be configured to perform any other suitable method.

2. Benefits

In specific examples, the system 100 and/or method 300 can confer several benefits over conventional methodologies used for detecting target substances in a sample. For example, conventional methodologies for allergen testing (e.g., mass spectroscopy, PCR techniques, standard ELISA, etc.), can be expensive, not currently suitable for consumer use, involve many processing steps, are unable to detect target proteins (e.g., that can cause an allergic response), and/or have limited accuracy. In specific examples, the system 100 and/or method 300 can perform one or more of the following:

First, the technology can provide an intuitive, consumer-friendly allergen testing device for detecting allergens in consumable samples while requiring minimal human interaction with the device. For example, the technology can perform detection of potentially life-threatening allergens while only asking the user to insert a consumable sample (e.g., a food sample, a drink sample, etc.) into a test container, seal the test container, and place the test container into an analysis device.

In a specific example, the user action of sealing the container (e.g., twisting a grinding cap with interior threads onto the test container) can simultaneously (1) seal the consumable sample opening, (2) grind the consumable sample opening at a first chamber, and (3) break a diaphragm situated between a first and second test container chamber, thereby releasing the magnetic diaphragm elements and the homogenized sample into the second chamber. Providing a grinding cap for dry grinding of the consumable sample can enable an easier homogenization process for certain food types. Additionally, consumable sample homogenization prior to wet mixing in the second chamber can enable more efficient and uniform reactions between the homogenized sample and processing reagents. In another specific example, the test container can define a keyed profile with asymmetric sides and/or ends of the test container, thereby ensuring that the test container can only be inserted into the analysis device in a single direction and/or angular orientation. Further, the technology can possess a form factor and design enabling discreteness and/or portability. For example, the technology can be handheld, mobile and/or possess a footprint enabling the technology to be easily transported (e.g., in a purse, in a pocket, in a backpack, etc.)

for on-the-go allergen testing (e.g., at a restaurant, at a workplace, etc.). In another example, mixing elements can be embedded in the diaphragm, so as to minimize loose mixing elements in the second chamber (e.g., a wet mix chamber). A lack of loose mixing elements rattling in the test container can minimize unnecessary noise and provide increased lifespan.

Second, the technology can additionally avoid excess components (e.g., minimize part count) by incorporating components serving multiple purposes in the functionality of the technology, in order to facilitate the desired ease-of-use and small form factor. For example, the test container can include a metallic diaphragm that acts both as a (1) retention element, obstructing sample flow from a grinding chamber (e.g., to grind a solid consumable sample into a homogenous sample for processing) to a mixing chamber (e.g., to mix a homogenous sample with a processing reagent for subsequent downstream analysis), and (2) as a mixing element (e.g., motivated by magnetically-driven rotation based on the diaphragm's magnetic properties) when the homogenized sample is in the mixing chamber. The diaphragm can optionally function as a force-generation element, wherein the diaphragm supports grinding features that generate a sample grinding force (e.g., to dry-grind the sample). Additionally or alternatively, in another example, the test container can include a grinding cap that acts as (1) a mechanism to grind a consumable sample into a homogenized sample for processing, (2) a sealing mechanism to prevent consumable sample backflow out of the test container, and (3) an actuating mechanism that applies a force (e.g., cracking force) to the metallic diaphragm, thereby transitioning the metallic diaphragm from retention mode to mixing mode. In examples, the technology can additionally or alternatively include disposable test containers including the requisite allergen detection materials, such that the technology can be used without cleaning, resetting, and/or refilling of test containers and/or analysis devices.

Third, the technology can quickly provide allergen testing results so as to provide a seamless eating experience. In a specific application, the technology can provide an indication and/or an analysis of presence of gluten in a food sample on the order of minutes (e.g., less than 3 minutes), using an improved allergen extraction process, streamlined and automatic sample processing, and an improved analysis protocol (e.g., using a detection substrate). However, variations of the specific application can additionally or alternatively involve detection of any other suitable type or number of allergens (e.g., gluten allergen, a dairy-derived allergen, a nut allergen, a fish allergen, an egg-derived allergen, a soy derived allergen, a peanut-derived allergen, shellfish-derived allergens, etc.) and/or any other substances of interest in a consumable sample, within any other suitable time frame, and/or using any other suitable substance indicator module.

Fourth, the technology provides an efficient, user-friendly device while detecting allergens with high specificity. In a specific application, the test container and analysis device can identify if a consumable sample has 20 parts per million (ppm) or more of gluten. Additionally or alternatively, the technology can identify any suitable combination or concentration of allergens, in order to detect allergens at a specificity matching FDA guidelines for restaurants to label consumables as free of a given allergen. Further, the technology can detect with such specificity while requiring a minimal amount of consumable sample, so as to not significantly remove portions of the consumable for other purposes (e.g., consumption).

Fifth, the technology can be designed to achieve the above-mentioned functionality while retaining an unobtrusive design. For example, the morphological form of a test container can be reduced by efficiently positioning and orienting components within the test container, while strategically directing sample flow through the components of the test container. In a specific example of efficient positioning of components, a capillary-flow based detection substrate can be positioned laterally adjacent to a grinding chamber situated above a mixing chamber. In a specific example of strategic directing of sample flow, the flow can include gravitationally driven flow along both the longitudinal axis and lateral axis of the test container in order to leverage both downward gravitational flow and upward capillary flow. Further, the technology can be assembled with materials complementing the strategic design. For example, the analysis device(s) and/or test container(s) can incorporate double shot plastics to improve durability while retaining functionality.

The technology can, however, provide any other suitable benefit(s) in the context of detecting target substances in consumable and/or non-consumable samples.

3. System

As discussed above, the system can include: a test container 105 that includes: a first chamber 110 for receiving the consumable sample, a driving element 120 configured to generate a homogenized sample upon processing of the consumable sample, a second chamber 130 configured to receive the homogenized sample and combine it with a process reagent to produce a dispersion, and analysis chamber 140 configured to expose the dispersion to a detection substrate 150 for detection of the harmful substance. As shown in FIGS. 17-18, an embodiment of a system 100 includes a test container 105 for detecting a target substance in a consumable sample, where the test container 105 defines a first chamber 110, and a second chamber 130, a magnetic diaphragm 160' situated between the first chamber 110 and the second chamber 130, the magnetic diaphragm 160' obstructing flow of the consumable sample, and the magnetic diaphragm 160' including one or more magnetic elements 163', 163" embedded in the magnetic diaphragm, and a driving element 120 geometrically complementary to the first chamber 110, the driving element including a consumable sample grinding feature extending from a surface of the driving element 120.

The test container 105 can be configured to couple to an analysis device (e.g., to cooperatively form an aligned system). In a specific example, the aligned system of the test container 105 coupled to the analysis device 205 can be characterized by a length less than 4 inches (e.g., a length of 3.5 inches), a width less than 1.5 inches (e.g., a width of 1.0 inches), and a height less than 3.5 inches (e.g., a height of 3.1 inches). In this specific example, the analysis device can possess substantially similar dimensions. In another specific example, the test container can be defined by a height less than 3 inches (e.g., a height of 2.5 inches). However, any suitable component of the system 100 can possess any suitable dimensions.

Components of the system 100 can be assembled and/or coupled (e.g., coupling between the test container 105 and the driving element 120, coupling between the test container 105 and the analysis device 205, detachable coupling between the diaphragm 160 and an interior wall of the first chamber 110 and/or second chamber 130, etc.) using sealants, press fitting, interference fits, tongue-and-groove interfaces, threaded interfaces, adhesives, ultrasonic welding, clips, and/or any other suitable mechanism.

In variations where the test container 105 can couple with the analysis device 205 in an alignment configuration 211 of an aligned system, the system 100 preferably operates when the system 100 is stood up on the base of the analysis device 205 (e.g., with the base physically against a non-system surface such as a table; with the base arranged at a non-zero angle to a gravity vector; etc.), as opposed to if the system 100 is lying on its face (e.g., a triangular face physically connected to the base of the analysis device 205; with the base arranged substantially parallel a gravity vector; etc.). Additionally or alternatively, the system 100 is operable in any orientation in the alignment configuration 211.

In relation to a weight of the system 100, components of the system 100 can have any suitable weight. In a specific example, the analysis device can possess a weight less than 2.5 oz, and the test container can possess a weight less than 0.85 oz, but any suitable component can have any suitable weight characteristic. Regarding materials of the system 100, components of the system 100 can be constructed with materials including: glass, metal, ceramic, plastic, or any other suitable material or combination thereof. In a specific example, components of the system 100 can be constructed using double shot plastics to enable durability.

In a variation, components of the system 100 can be waterproof and/or water-resistant. In an example, components of the system 100 with surfaces exposed to interaction with a consumable sample can be coated with a water-repellant coating. In another example, the system 100 can include waterproofing sealants such as gaskets, o-rings, and/or other suitable waterproofing components. In a specific example, the test container 105 can include a waterproofing sealant arranged at the first chamber 110 along the circumference of the consumable reception opening 112, such that waterproofing sealant can act as a sealing intermediary between the first chamber 110 and the driving element 120 in response to coupling of the a first chamber 110 and the driving element 120 by the user. Additionally or alternatively, components of the system 100 can maintain functionality upon exposure of different components of the system to different types of consumable samples (e.g., of varying viscosity, chemicals, liquid, solid, gas, etc.). However, the system 100 can include any suitable waterproofing element and components of the system 100 can have any suitable resilience.

However, the system 100 can possess any suitable mechanical characteristic.

3.1 System—Test Container

As noted above and shown in FIGS. 1 and 2A-2B, in an embodiment, the test container 105 includes: a first chamber 110 for receiving the consumable sample, a driving element 120 configured to generate a homogenized sample upon processing of the consumable sample, a second chamber 130 configured to receive the homogenized sample and combine it with a process reagent to produce a dispersion, and analysis chamber 140 configured to expose the dispersion to a detection substrate 150 for detection of the harmful substance.

Regarding test chamber components, the first chamber 110, the second chamber 130, and the analysis chamber 140 (e.g., a detection substrate 150 of an analysis chamber 140) preferably defines a consumable sample fluid path through the test container 105. The consumable sample can preferably be characterized by different phases (e.g., solid phase, liquid phase, gaseous phase) throughout the sample fluid path. For example, a solid consumable sample can be received at a consumable reception opening 112 of the first chamber 110. Upon grinding of the solid consumable sample in the first chamber 110, and mixing of the homogenized consumable sample in the second chamber 130, the consumable sample is preferably in a liquid dispersion phase for transfer to a detection substrate 150 of an analysis chamber 140. However, the consumable sample can have any suitable phase along the sample fluid path. Consumable sample and/or other fluid flow through the sample fluid path can be gravitationally driven, magnetically driven, capillary driven, pressure driven, and/or driven through any suitable mechanism. However, flow characteristics of the sample and/or the sample fluid path can be configured in any suitable manner.

However, the test container 105 and/or components of the test container 105 can possess any suitable characteristics.

3.1.A Test Container—First Chamber

The first chamber 110 functions to receive and facilitate processing (e.g., homogenization) of a consumable sample that the user intends to analyze for presence of a harmful substance (e.g., an allergen). In an embodiment, the first chamber 110 preferably includes a consumable reception opening 112 configured to receive the consumable sample from the user, and a second opening 114 configured to deliver a homogenized sample generated from the consumable sample into the second chamber 130 for further processing. In a specific example, the first chamber 110 can define a consumable reception opening 112 and a second opening 114 opposing the consumable reception opening 112. In another specific example, a first chamber 110 can be positioned proximal the test container top 106. However, the first chamber 110 can be positioned at any suitable location relative any suitable component of the system 100.

The consumable reception opening 112 can be configured to passively receive the consumable sample, or can additionally or alternatively be configured to actively facilitate reception of the consumable sample, for instance, by transmitting a positive/negative pressure at the consumable reception opening 112 that drives the consumable sample into the first chamber 110, by providing a mechanism (e.g., scooping mechanism, suction mechanism) that guides the consumable sample into the consumable reception opening 112, and/or by providing any other suitable mechanism for active delivery of the consumable sample into the first chamber 110. The consumable reception opening 112 is preferably at a superior portion of the first chamber 110, in the orientation shown in FIGS. 2A and 2B, such that gravity facilitates transfer of the consumable sample, during processing, toward a second chamber 130 inferior to the first chamber 110; however, the consumable reception opening 112 can alternatively be configured at any other suitable location along the length of the first chamber 110. Additionally or alternatively, transfer of samples and/or process reagents throughout the system 100 can be facilitated with pressurization or any other suitable means of driving material (e.g., such that gravitational force is not required). Furthermore, in examples, the consumable reception opening can include features (e.g., a sloped entryway into the first chamber 110, a wide mouth relative to other portions of the interior of first chamber 110) that facilitate reception of the consumable sample. Additionally or alternatively, the consumable reception opening 112 and/or any other portion of the first chamber 110 can include a feature that facilitates control of an amount of a consumable sample that is processed using the test container 105, prior to and/or after reception of the consumable sample within the first chamber 110. For instance, the first chamber can include a maximum and/or minimum fill line to guide delivery of the consumable sample into the first chamber 110 between a maximum and/or minimum range of amounts. In another example, portions of the test container 105 can be configured to exclude or accommodate a larger than desired volume of a consumable sample (e.g., by distributing excess volumes of the consumable sample into another portion of the system 100, or by expelling excess volumes of the consumable sample from the system 100). In another example, the first chamber 110 can additionally or alternatively include a sensor (e.g., a weight sensor, a light sensor, etc.) configured to measure aspects of a consumable sample received through the consumable reception opening 112 of the first chamber 110. The first chamber can additionally or alternatively include a user indicator element in communication with the sensor, the user indicator element configured to present a user indicator that indicates whether a sufficient and/or excess amount of consumable sample has been placed in the first chamber 110 to the user. In a specific example, the first chamber can include a weight sensor configured to measure the weight of the consumable sample in the first chamber 110, where a user indicator element of the first chamber can present a user indicator (e.g., "too much," a sad face, etc.) in response to the measured weight exceeding a threshold weight. In examples, the consumable reception opening 112 can have a diameter or width between 10 and 20 mm; however, the consumable reception opening can alternatively have any other suitable dimensions.

The consumable sample is preferably a food sample potentially containing a harmful substance (e.g., an allergen), and is preferably an unprocessed food sample, such that the user can gather an insubstantial volume of a food substance that he/she intends to consume for a meal, and deliver it into the consumable reception opening 112 of the test container 105 for processing and analysis. In this example, the food sample can include a mixture of different food items (e.g., different components of an entrée), can include a single food item (e.g., a single component of an entrée), and/or can include a sequence of different food items (e.g., a sequence of components from an entrée). The food sample can be cored, spooned, tweezed, and/or processed from a bulk volume of food in any other suitable manner. However, in variations, the consumable sample can include any one or more of a: beverage sample (e.g., volume of a mixed drink), cosmetic substance (e.g., volume of makeup, volume of lotion, volume of fragrance, volume of soap, etc.), and any other sample potentially containing a substance that is harmful to the user. In variations, the consumable sample can have a volume of between 1 and 7 mL prior to processing within the first chamber 110; however, the consumable sample can alternatively have any other suitable volume.

The second opening 114 functions to deliver a homogenized sample (e.g., entirely homogenized, substantially homogenized, etc.) generated from the consumable sample into the second chamber 130 for further processing. The second opening 114 is preferably at an inferior portion of the first chamber 110 relative to the consumable reception opening, in the orientation shown in FIGS. 2A and 2B, such that gravity facilitates transfer of the consumable sample, during processing, toward a second chamber 130 inferior to the first chamber 110; however, the second opening 114 can alternatively be configured at any other suitable location along the length of the first chamber 110. Furthermore, in examples, the second opening 114 can include features (e.g., a sloped entryway into the second chamber 130, a wide mouth relative to other portions of the interior of first chamber 110) that facilitate delivery of the consumable sample out of the first chamber 110. In examples, the second opening 114 can have a diameter or width between 10 and 20 mm; however, the consumable reception opening can alternatively have any other suitable dimensions.

The first chamber 110 preferably defines an internal enclosed cavity open only at the consumable reception opening 112 and the second opening 114, in order to facilitate processing of the consumable sample, within the first chamber 110, in a desired direction. However, the first chamber 110 can additionally or alternatively include venting and/or metering features that facilitate processing of the consumable sample in a controlled manner. The volume of the first chamber 110 is preferably substantially small, in order to contribute to the compactness of the test container, and in order to accommodate a small volume of the consumable sample, such that the user does not feel as though he/she is sacrificing a sufficient portion of his/her food. In variations, the first chamber 110 has an internal volume of between 1 and 7 mL between the consumable reception opening 112 and the second opening 114; however, the first chamber 110 can alternatively define any other suitable volume.

Figure 2A:
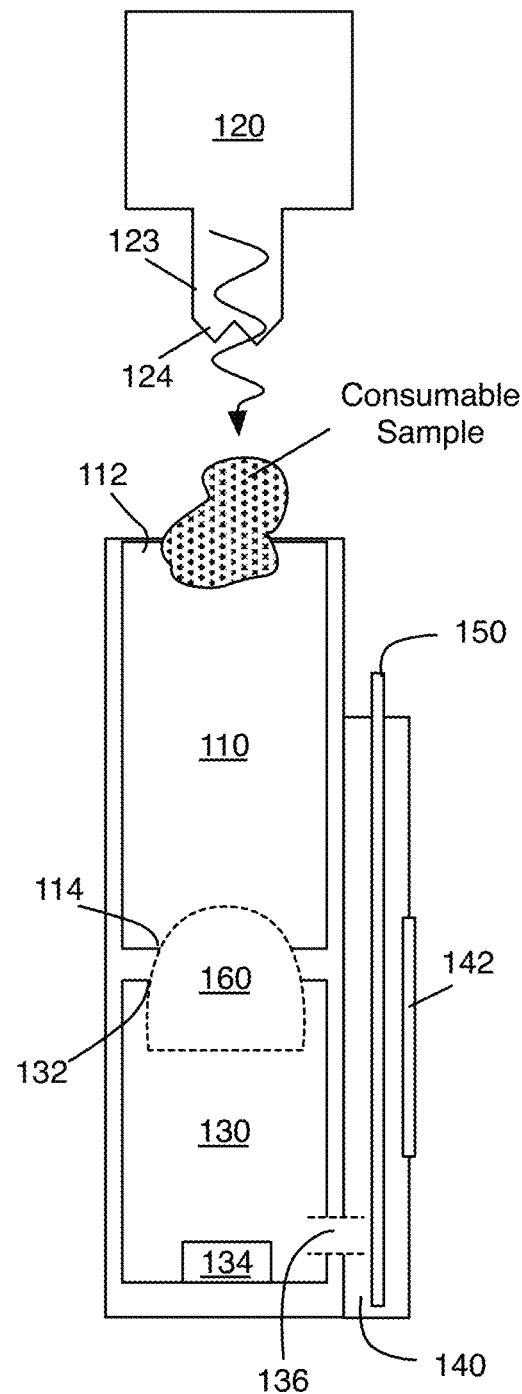
FIGS. 2A and 2B depict embodiments and variations of a portion of a system for detection of harmful substances.
Figure 2B:
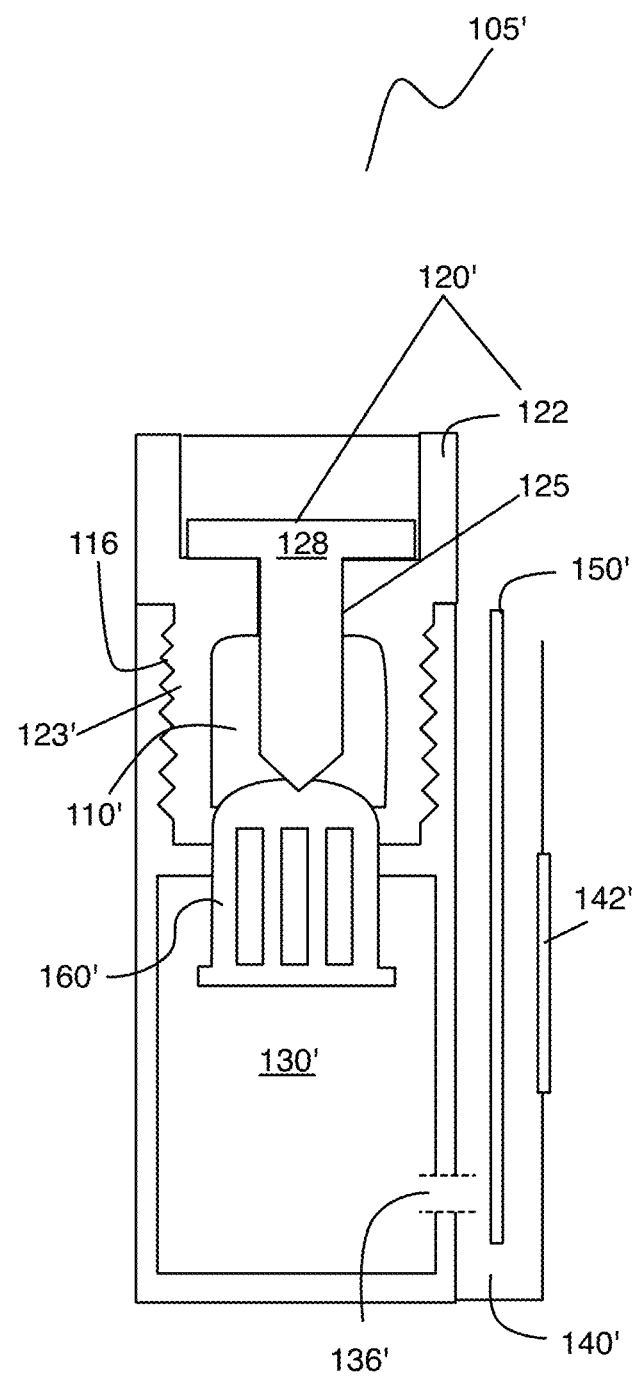

In morphology, the internal cavity of the first chamber 110 preferably has a uniform cross section over a majority of the length of the first chamber 110, in order to facilitate processing of the consumable sample in a uniform manner throughout the length of the first chamber 110; however, the cross section of the first chamber 110 can alternatively be non-uniform. Additionally, the internal cavity of the first chamber 110 preferably includes features that facilitate processing of the consumable sample by other elements of the test container 105 (e.g., the driving element 120), as described in further detail below. As such, in one example, an interior portion (e.g., wall) and/or an exterior portion (e.g., exterior surface) of the first chamber 110 can include threads 116, as shown in FIG. 2B, that facilitate screwing of a driving element 120 within/about the first chamber 110 in processing the consumable sample toward the second opening 114. In another example, an interior portion or exterior portion (e.g., wall, surface) of the first chamber 110 can be substantially smooth and/or have low friction to facilitate sliding of a driving element 120 between the consumable reception opening 112 and the second opening 114 of the first chamber 110. The first chamber 110 can, however, include any other suitable features that facilitate processing of the consumable sample in cooperation with another element (e.g., a driving element) of the system 110. For instance, the first chamber 110 can include a fill line configured to guide a user in providing a desired amount of the consumable sample (e.g., such that an amount of the consumable sample provided by the user is above a lower critical limit and below an upper critical limit).

In a variation, the first chamber can house a mixing reagent facilitating homogenization of the consumable sample in the first chamber 110 (e.g., by a grinder 122 of a driving element 120). Mixing reagents can include water, a processing reagent, saline, and/or any suitable reagent facilitating consumable sample homogenization and/or downstream processing of the consumable sample (e.g., at an analysis chamber 140). The mixing reagent is preferably housed in the first chamber 110 prior to reception of the consumable sample through the consumable reception opening 112, but can additionally or alternatively be introduced into the first chamber 110 during reception of the consumable sample into the first chamber 110, and/or after reception of the consumable sample into the first chamber 110. In a specific example, mixing reagent can be contained within a diaphragm 160 positioned between the first chamber 110 and the second chamber 130, where the diaphragm 160 can define mixing reagent holes (e.g., at a roof 164 and/or broad face of the diaphragm 160) configured to facilitate movement of the mixing reagent from the diaphragm 160 into the first chamber 110. In another specific example, mixing reagent can be contained with the interior walls of the first chamber 110 defining the internal cavity of the first chamber 110, where the interior walls can include one or more mechanisms facilitating introduction of mixing reagent into the first chamber 110 at any suitable time (e.g., port holes for user reagent injection, reagent-containing pods within the interior walls that rupture upon cap tightening, etc.). However, the first chamber 110 can include any suitable structural elements for facilitating interaction between the consumable sample and mixing reagent at the first chamber 110.

However, the first chamber 110 and/or components of the first chamber 110 can be configured in any suitable fashion.

3.1.B Test Container—Driving Element

Figures 3A, 3B:
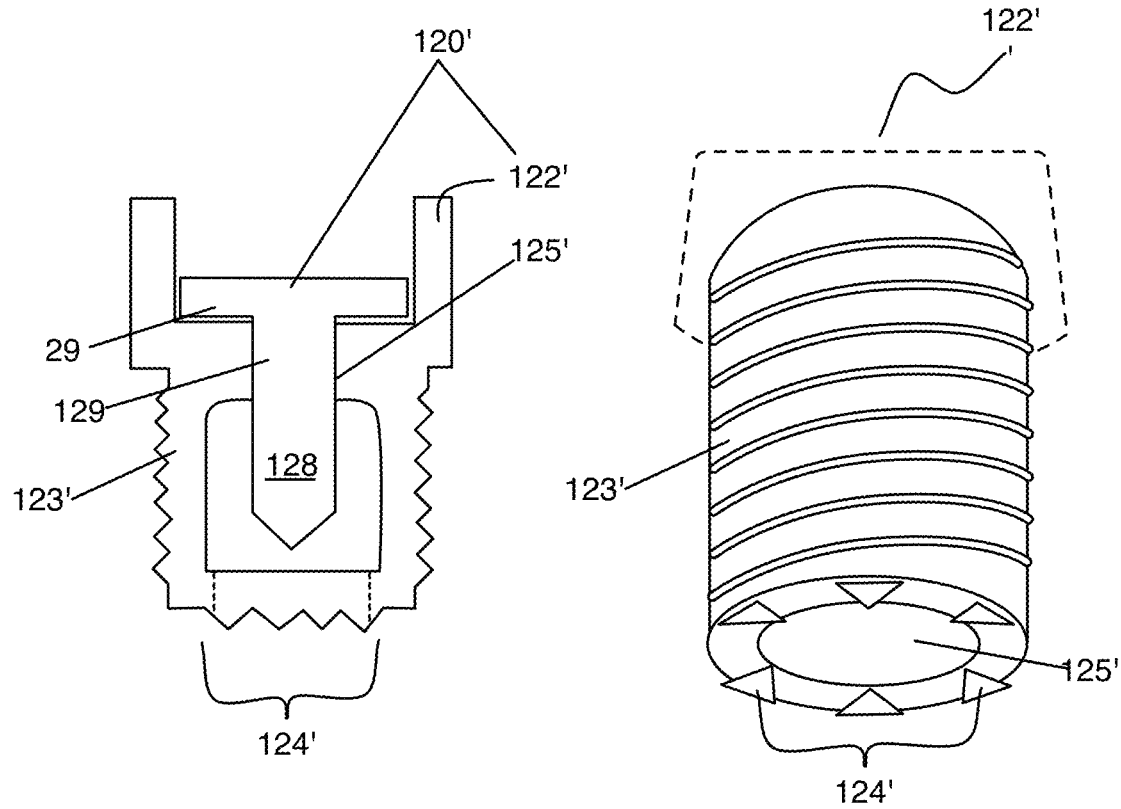
FIGS. 3A and 3B depict first variations and examples of a portion of a system for detection of harmful substances.

The driving element 120 (e.g., test container cap) functions to interact with the first chamber and to facilitate generation of a homogenized sample upon processing of the consumable sample toward the second opening 114 of the first chamber 110. As such, the driving element 120 preferably has a morphological form that complements or mates with a morphological form of the first chamber 110 (e.g., an interior morphology of the first chamber, an exterior morphology of the first chamber) in providing a mechanism that transforms the consumable sample into a homogenized sample. In a specific example, the driving element 120 is geometrically complementary to the first chamber 110. Preferably, the driving element 120 has a portion (e.g., shaft 123) that interacts with an interior portion of the first chamber 110, as shown in FIGS. 2B and 3A-3B, wherein relative motion between the first chamber 110 and the driving element 120 is guided (e.g., constrained) by the morphological forms of the first chamber 110 and the driving element 120. In a specific example, the driving element includes a shaft 123 having a radius smaller than a radius of the consumable reception opening 112. The driving element can optionally include a head that functions to seal the consumable reception opening 112. The head can have a critical dimension (e.g., radius) larger than the inner radius and/or outer radius of the first chamber, or have any other suitable dimension. The driving element head can additionally or alternatively be sized for closure of the consumable reception opening 112. The head can be arranged along an end of the shaft, preferably along the end of the shaft opposing the hollow channel opening, but can alternatively be arranged in any other suitable location.

In variations, the driving element 120 includes a grinder 122 and a plunger 128, as described below and shown in FIGS. 2A-2B and 3A-3B, however, other variations of the driving element 120 can adapt elements or features of the grinder 122/plunger 128 in enabling processing of the consumable sample, and/or be configured in any other suitable manner.

The grinder 122 functions to grind the consumable sample within the first chamber 110 during relative motion between the driving element 120 and the first chamber 110, in order to produce a homogenized sample with approximately uniformly sized particles. The homogenized sample is then distributed into the second chamber 130 for further processing with a process reagent, and analysis using a detection substrate 150. In one variation, the grinder 122 includes a shaft 123 and a set of protrusions 124 coupled to the shaft 123, and is configured to grind the consumable sample during processing of the consumable sample between the consumable reception opening 112 and the second opening 114 of the first chamber 110. In a specific example, the driving element 120 can include a protrusion 124 (e.g., a consumable sample grinding feature) protruding from a surface of the driving element 120. Preferably, the shaft 123 is configured to translate within the interior portion of the first chamber 110 (e.g., with sliding motion, with rotational motion that produces translation), and the set of protrusions 124 is configured to grind up the consumable sample as the shaft 123 rotates and/or translates within the first chamber 110. As such, translation/rotation of the grinder 122 relative to the first chamber 110 moves portions of the consumable sample between protrusions of the set of protrusions 124, thereby grinding the consumable sample. The shaft 123 can also include a channel 125 (e.g., a hollow channel concentrically aligned with the shaft) to accommodate a plunger that enables driving of the homogenized sample from the first chamber 110 to the second chamber 130; however, the shaft 123 can alternatively omit a channel 125 and be substantially solid. The protrusion 124 preferably extends from an interior surface of the driving element 120 (e.g., from the channel surface), but can alternatively extend from an exterior surface (e.g., from a major sidewall face, from a shaft end, etc.) or any other suitable surface of the driving element. In a specific example, the driving element 120 can include a consumable sample grinding feature (e.g., a protrusion 124) physically connected to an interior surface of the hollow channel 125, wherein the consumable sample grinding feature extends away from the interior surface of the hollow channel 125. The protrusion 124 can extend parallel the shaft longitudinal axis, perpendicular the shaft longitudinal axis, at any suitable angle to the shaft longitudinal axis, spiral along the interior of the hollow channel (e.g., about the shaft longitudinal axis), or be arranged in any other suitable configuration. The protrusion 124 can be shorter than the shaft length, longer than the shaft length, or have any other suitable length or dimension.

In this variation, the set of protrusions 124 preferably includes protrusions having sharp points and/or a rough surface, in order to facilitate grinding of the consumable sample. In another variation, the grinder 122 can include a set of protrusions with pointed edges for grinding one or more consumable samples in a solid phase (e.g., as opposed to a liquid or gaseous phase). Furthermore, the set of protrusions 124 can be arranged in a pattern (e.g., a radial pattern, a rectangular pattern) with respect to a surface of the shaft 123. Furthermore, the set of protrusions 124 preferably has a small inter-protrusion spacing (e.g., between 0.1 mm to 0.5 mm). However, the set of protrusions 124 can alternatively be arranged in a random manner and/or in any other suitable manner.

In one example of this variation, as shown in FIGS. 3A-3B, the grinder 122' includes an set of protrusions 124' arranged in a uniform radial distribution at an inferior surface of a shaft 123' having a concentric channel 125', wherein each protrusion defines a wedge-shaped footprint having a sharp point pointing toward the channel 125' of the shaft. In this example, the set of protrusions 124' includes 6 wedge-shaped protrusions; however, variations of this example can include any other suitable number of protrusions (e.g., between 4 and 12 protrusions) defining any other suitable morphology. Furthermore, in this example, the shaft includes exterior threads 121 configured to enable translation of the shaft 123 within the first chamber 110', as the shaft rotates in cooperation with mating threads 116 within the interior of the first chamber 110'. As shown in FIG. 17, in a specific example, the driving element 120 can include a threaded shaft 123 including threads 121 along the exterior surface of the threaded shaft 123, and wherein a driving element feature (e.g., a protrusion 124, a plunger 128, etc.) protrudes parallel a longitudinal axis of the driving element. However, variations of this example of the grinder 122' can include protrusions having a non-uniform and/or a non-radial arrangement. Furthermore, the shaft and the first chamber 110 can be alternatively configured such that mating threads 116 at an exterior surface of the first chamber are configured to mate with a portion of the grinder 122' in order to facilitate relative motion between the grinder 122' and the first chamber 110 during grinding.

In another variation, as shown in FIGS. 4A and 4B, the grinder 122 includes a set of protrusions 124 at an interior surface 126 of the grinder 122, wherein the interior surface 126 is configured to be parallel to a corresponding surface within the first chamber 110. As such, in this variation, translation and/or rotation of the grinder 122 about/within the first chamber 110 moves portions of the consumable sample between protrusions of the set of protrusions 124, thereby grinding the consumable sample. The grinder 122 in this variation includes a plunger opening 127 configured to accommodate a plunger that enables driving of the homogenized sample from the first chamber 110 to the second chamber 130; however, the grinder 122 can alternatively omit a plunger opening 127 and be substantially solid. In this variation, the set of protrusions 124 preferably includes protrusions having sharp points and/or a rough surface, in order to facilitate grinding of the consumable sample. Furthermore, the set of protrusions 124 can be arranged in a pattern (e.g., a radial pattern, a rectangular pattern) with respect to the interior surface 126 of the grinder 122 (e.g., about an opening 127 in the grinder 122), or arranged in any other suitable manner.

In one example of this variation, as shown in FIGS. 4A and 4B, the grinder 122" includes an set of protrusions 124" arranged in a uniform radial distribution at an interior surface having a concentric plunger opening 127", wherein each protrusion defines a wedge-shaped footprint having a sharp point pointing toward the plunger opening 127" of the interior surface 126". In this example, the set of protrusions 124" includes 5 wedge-shaped protrusions; however, variations of this example can include any other suitable number of protrusions (e.g., between 4 and 12 protrusions) defining any other suitable morphology. Furthermore, in this example, the grinder 122" includes interior threads configured to enable translation of the grinder 122" about an exterior portion of the first chamber 110", as the shaft rotates in cooperation with mating threads at the exterior portion of the first chamber 110".

In another example of this variation, as shown in FIG. 17, the shaft 123 can include one or more shearing protrusions 124" configured to apply a shearing force on the consumable sample and/or the diaphragm 160. In a specific example, the shaft 123 can include an end defining a channel opening of a hollow channel 125 of the shaft 123 (e.g., wherein the hollow channel and/or shaft terminate in the channel opening), wherein the end of the shaft 123 includes a set of shearing protrusions 124 extending along a longitudinal axis of the shaft 123, and wherein a length of the shaft 123 with the shearing protrusions 124" can be greater than a length of the first chamber 110 (e.g., a length extending from the consumable reception opening 112 to the magnetic diaphragm 160' along the longitudinal axis of the test container 105). The shearing protrusions are preferably configured to align with the frangible region of the diaphragm, but can be otherwise arranged. In one example, the radius of the arcuate region defined by the shearing protrusions is preferably substantially equal to the radius of the frangible region 161, but can alternatively be larger or smaller. Additionally or alternatively, a set of shearing protrusions 124" can have any suitable orientation in relation to components of the test container 105 (e.g., extend radially outward from the shaft end, extend radially inward from the shaft end, etc.). In this example, the driving element 120 can additionally or alternatively include a set of grinding protrusions 124' (e.g., extending from an interior surface of the shaft 123, extending from an interior surface of the channel 125, etc.). However, a grinder 122 including a set of shearing protrusions can be otherwise configured.

Other variations of the grinder 122 can additionally or alternatively operate using any other suitable mechanism. For instance, the grinder 122 can operate by one or more of: forcing the consumable sample through a screen (e.g., a mesh screen), crushing the consumable sample (e.g., as in a pill crusher), processing the consumable sample (e.g., with a blade), grinding the consumable sample (e.g., with a mortar-and-pestle, with a grinding barrel, etc.), or in any other suitable manner.

The plunger 128 (e.g., plunging element 128) functions to facilitate driving of homogenized portions of the consumable sample into the second chamber 130 after and/or during processing by the grinder 122. The plunger 128 can optionally function as a cracking force generator, and function to break the diaphragm into one or more constituent pieces. In variations of the test container 105 including a diaphragm 160, the plunger 128 can additionally or alternatively function to transition the diaphragm 160 between a first configuration and a second configuration, as described in further detail below. In a variation shown in FIG. 3A, the plunger 128 can include a plunger shaft 129 and a stop 29, wherein the plunger shaft 129 is configured to pass through a channel 125 or plunger opening 127 of the grinder 122, in order to facilitate driving of the homogenized sample into the second chamber 130. The stop 29 is then configured to constrain a range of motion of the plunger 128, such that the plunger cannot pass entirely into the first chamber in an uncontrolled manner. Preferably the plunger shaft 129 is a cylindrical shaft; however, the plunger shaft 129 can alternatively have any other suitable cross-section or profile configured to facilitate driving of the homogenized sample into the second chamber 130, in cooperation with the grinder 122. In particular, an inferior portion of the plunger shaft 129 can be blunt (e.g., hemispherical, planar), sharp (e.g., conical, pyramidal), or have any other suitable morphology for driving of the homogenized sample into the second chamber 130. The stop 29 preferably has a larger governing dimension than the plunger shaft 129 to provide the constrained range of motion; however, in other variations, the stop 29 can include protrusions (e.g., tabs) extending from a surface of the plunger shaft 129, thereby obstructing motion of the plunger shaft 129 into the channel 125/plunger opening 127 past the stop 29. The plunger 128 can be coupled to the grinder, can be distinct from the grinder 122, or can be configured to interface with the grinder 122 in any other suitable manner. In one example, the plunger 128 includes a cylindrical plunger shaft 129 configured to slide within a channel 125/plunger opening 127 of the grinder 122, and the stop 29 includes a plate coupled to a superior portion of the plunger shaft 129, having a diameter wider than that of the plunger shaft 129 to constrain a range of motion of the plunger shaft 129. In a specific example, the plunging element 128 can extend along a longitudinal axis of the shaft, wherein a length of the plunging element 128 can be greater than a length of the first chamber 110 (e.g., a length from the consumable reception opening 112 to the magnetic diaphragm 160' along the longitudinal axis of the test container 105), where a tip of the plunging element 128 physically applies a force to the diaphragm 160 as a user couples the driving element 120 to the first chamber 110 (e.g., screws the driving element 120 onto the first chamber 110, seals the consumable reception opening 112 of the first chamber 110 with the driving element 120, etc.). In one variation, the tip of the plunging element can be substantially aligned with a frangible region of the diaphragm. However, the plunging element 128 can be configured in any suitable fashion.

In a variation of the plunger 128, the plunger 128 can be a sprung plunger (e.g., spring-loaded plunger) operable between a compressed configuration and/or extended configuration and a resting configuration (e.g., equilibrium length), wherein transition from the compressed configuration to the resting configuration can result in an applied mechanical force to the diaphragm 160 (e.g., a roof 164 of the diaphragm 160 and/or consumable sample. The applied mechanical force can break the diaphragm 160 (e.g., at a frangible region of the diaphragm 160), deform the diaphragm 160, transition the diaphragm 160 from a first configuration (e.g., a retention mode obstructing flow of the consumable sample through the second opening 114) to a second configuration (e.g., a mixing mode for facilitating mixing of the consumable sample with a processing reagent within the second chamber 130), and/or satisfy any suitable purpose. In a specific example, the plunging element 128 can define a sharp tip, and the plunging element 128 can be in a spring-loaded configuration substantially within the hollow channel 125 and oriented towards a channel opening defined by the shaft. In this variation, when the driving element 120 is mated with the first chamber 110, the length of the plunger in the compressed configuration can fall short of physically touching the diaphragm 160, and the length of the plunger in the resting configuration can extend beyond a broad face (e.g., facing the consumable reception opening 112) of the diaphragm 160. Additionally or alternatively, other components of the driving element 120 can be spring-loaded to facilitate homogenization of the consumable sample in the first chamber 110, application of a force to the diaphragm 160, and/or for any suitable purpose.

In other variations, elements of the grinder 122 can additionally or alternatively be distributed within the first chamber 110, such that the first chamber 110 includes elements that actively enable grinding of the consumable sample. For instance, an inferior surface of the first chamber 110 can include at least a subset of the set of protrusions 124, such that movement of the grinder 122 processes the consumable sample in cooperation with protrusions within the first chamber. In some variations, a plunger 128 can be replaced by a driving module (e.g., configured to provide positive and/or negative pressure within the test container, configured to centrifuge the test container, etc.) that facilitates delivery of the homogenized sample throughout the test container in a controlled manner. In still other variations, however, the driving element 120 can omit the grinder 122, the plunger 128, and/or any other features configured to process a solid and/or non-homogenous consumable sample (e.g., beverage, cosmetic, etc.), which would not require grinding within a first chamber 110 prior to reception at a second chamber. As such, in some variations of the system 100, the first chamber 110, the driving element 120, and/or the second chamber 130 can be configured in manners that are appropriate to processing of consumable samples, based upon the form(s) of the consumable samples.

In a variation of the driving element 120, the driving element 120 can include a vacuum cavity. The vacuum cavity can be arranged at the head of the driving element 120 (e.g., at a driving element head region distal a shaft 123, at the driving element head region offset from the shaft, etc.), arranged along a side of the test container, or be arranged in any other suitable location. The vacuum cavity is preferably configured to align with an analysis chamber 140 of the test container 105 when the driving element 120 is mated with the first chamber 110, but can alternatively be misaligned. The vacuum cavity can include a cavity bottom proximal a shaft 123 of the driving element 120, wherein the cavity bottom is proximal an analysis chamber 140 of the test container 105 in the mating configuration of the driving element 120 and test container 105. The cavity bottom can define one or more fluid vacuum holes configured to align with one or more holes of the analysis chamber 140 in the mating configuration. The one or more fluid vacuum holes can facilitate pressure stabilization in the analysis chamber 140 and/or can drive a consumable sample (e.g., in a dispersion form) through the analysis chamber 140 (e.g., aiding the capillary flow rate through a detection substrate 150 of the analysis chamber 140). However, the driving element 120 can include any suitable cavities configured to facilitate any suitable phenomenon.

However, the driving element 120 and/or components of the driving element 120 can include be configured in any suitable fashion.

3.1.C Test Container—Second Chamber

As shown in FIGS. 15 and 18, the second chamber 130 functions to receive the homogenized sample after processing within the first chamber 110, to facilitate combination of the homogenized sample with a process reagent to produce a dispersion, and to facilitate delivery of the dispersion from the second chamber 130 for further analysis to detect a harmful substance. Preferably, the second chamber 130 includes a sample reception opening 132 and an outlet port 136 configured to facilitate delivery of the dispersion to a detection substrate, as shown in FIG. 2A. In some variations, the second chamber 130 can further include a mixing element 134 configured to cooperate with a mixing module (e.g., of an analysis device 205 in communication with the test container), to facilitate mixing of the homogenized sample with the process reagent in the second chamber 130. However, the second chamber 130 can additionally or alternatively include any other suitable elements and/or be configured in any other suitable manner for generation of a dispersion from the homogenized sample.

As shown in FIGS. 15 and 18, in relation to the test container body, the second chamber is preferably proximal the test container bottom 107. Alternatively, the second chamber 130 can be adjacent to positioned at, proximal to, adjacent to, near, distanced from, and/or possess any suitable positional relationship to the test container body and/or other components of the test container 105 and/or analysis device 205. In relation to the first chamber 110, the second chamber 130 is preferably configured to couple to the first chamber 110, and in variations, can include a unitary construction with the first chamber, can be physically coextensive with the first chamber 110, and/or can be coupled to the first chamber 110 in any other suitable manner. Furthermore, the second chamber 130 is preferably inferior to the first chamber 110, such that gravity facilitates transfer of the homogenized sample from the first chamber 110 toward the second chamber 130 in the orientation shown in FIG. 2A.

As shown in FIGS. 15 and 18, in one variation, the second chamber 130 is aligned with the first chamber 110 along a longitudinal axis of the test container body. In an embodiment of this variation, the first and second chambers are aligned with the consumable reception opening 112, second opening, sample reception opening 132, and test container bottom and/or second chamber bottom each normal the test container body longitudinal axis. However, the openings can be otherwise arranged. In a second variation, the first and second chambers are aligned along the test container body lateral axis. In this variation, the consumable reception opening 112 can be parallel, normal, or at any other suitable angle to the test container body longitudinal axis. However, the openings can be otherwise arranged. In a third variation, the first and second chambers can be fluidly connected by an intervening fluid manifold, wherein the fluid manifold can connect the second opening to the sample reception opening. The fluid manifold can have the same or different cross section as that of the second opening and/or the sample reception opening, or have any other suitable cross section. The fluid manifold can be straight, curved, bent, boustrophedonic, or have any other suitable configuration.

Alternatively, the first and second chambers can be aligned along any suitable axis (e.g., lateral axis), plane, and/or angle related to the test container 105 and/or components of the test container 105. However, the second chamber can alternatively be configured adjacent to or in any other suitable location relative to the first chamber 110 in alternative variations of the system 100.

The sample reception opening 132 can be configured to passively receive the homogenized sample, or can additionally or alternatively be configured to actively facilitate reception of the homogenized sample, for instance, by transmitting a positive/negative pressure at the sample reception opening 132 that drives the homogenized sample into the second chamber 130, by providing a mechanism (e.g., scooping mechanism) that guides the homogenized sample into the sample reception opening 132, and/or by providing any other suitable mechanism for active delivery of the homogenized sample into the second chamber 130. The second chamber 130 can define a sample reception opening 132 coextensive with (e.g., coinciding) the second opening 114 of the first chamber 110. Additionally or alternatively, the sample reception opening 132 and/or other openings defined by the second chamber 130 can be coextensive, fluidly connected, and/or fluidly contiguous with any suitable opening of components of the test container 105 and/or analysis device 205. Additionally or alternatively, portions of the test container 105 and/or system 100 can be configured to facilitate delivery of contents from the first chamber 110 into the second chamber 130. For instance, a portion of the driving element 120 (e.g., the plunger 128) can include a module (e.g., syringe pump, fluid delivery element) that applies positive pressure and/or delivers a wash solution from the first chamber 110 to the second chamber 130, in order wash portions of the homogenized sample into the second chamber 130. The sample reception opening 132 is preferably at a superior portion of the second chamber 130, in the orientation shown in FIG. 2A, such that gravity facilitates transfer of the homogenized sample, during processing, into the second chamber 130 in cooperation with the driving element 120; however, the sample reception opening 132 can alternatively be configured at any other suitable location along the length of the second chamber 130. Furthermore, in examples, the sample reception opening can include features (e.g., a sloped entryway into the second chamber 130, a wide mouth relative to other portions of the interior of second chamber 130) that facilitate reception of the homogenized sample. In examples, the consumable reception opening 112 can have a diameter or width between 10 and 20 mm; however, the sample reception opening can alternatively have any other suitable dimensions.

In variations, the sample reception opening 132 is preferably configured to facilitate transitioning of a diaphragm 160, configured to facilitate delivery of the homogenized sample into the second chamber 130, between a first configuration and a second configuration, as described in further detail below; however, the sample reception opening 132 can alternatively be configured to facilitate delivery of the homogenized sample into the second chamber 130 from the first chamber 110 without a diaphragm 160, for instance, by way of a valve (e.g., one-way valve, two-way valve) configured between the first chamber 110 and the second chamber 130. Alternatively, the sample reception opening 132 can be configured to directly transfer the homogenized sample from the first chamber 110 to the second chamber 130 without any intermediate element(s).

Figure 5:
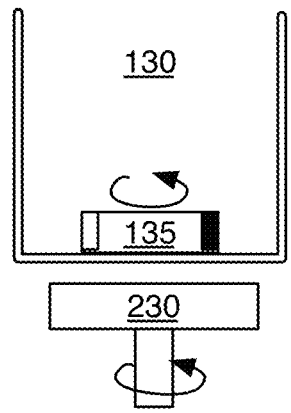
FIG. 5 depicts an example of a portion of a system for detection of harmful substances.

In some variations, the second chamber 130 can include a mixing element 134 that functions to facilitate mixing of the homogenized sample with a process reagent within the second chamber 130. The mixing element 134 can be disposed within the second chamber 130, and/or can be coupled to the second chamber 130 in any other suitable manner. The mixing element 134 is preferably configured to cooperate with a mixing module 230 of an analysis device 205, as described in further detail below, such that the mixing element 134 and the mixing module 230 complement each other to provide a mixing mechanism within the second chamber 130; however, variations of the system 100 can entirely omit the mixing element 134 and/or the mixing module 230 and facilitate combination of the homogenized sample with the process reagent in any other suitable manner (e.g., the process reagent can be combined with the consumable sample during processing within the first chamber 110). In variations, the mixing element 134 can provide any one of: a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example, as shown in FIG. 5, the mixing element 134 includes a magnet 135 (e.g., magnetic stir bar) configured within the second chamber 130 that is configured to magnetically couple to a complementary magnet of a mixing module 230. In the example, the complementary magnet can be coupled to a spinning motor, thereby producing rotation at the magnet 135 within the second chamber 130. In variations of the example, the magnet 135 can include a permanent magnet and/or an electromagnet. Furthermore, the magnet 135 can be a distinct element within the second chamber 130, or can additionally or alternatively be coupled to or integrated with a diaphragm 160 configured to access the second chamber 130, as described below. Furthermore, variations of the example can include any suitable number of magnets 135 of the second chamber 130.

In variations, the second chamber 130 can be prepackaged with the process reagent (e.g., where the second chamber 130 houses a processing reagent), such that the homogenized sample is automatically brought into contact with the process reagent upon transmission between the first chamber 110 and the second chamber 130. Additionally or alternatively, the second chamber 130 and/or any other suitable portion of the test container 105 can include or be coupled to a fluid delivery module (e.g., of the analysis device 205, of the test container 105, etc.) for reception of the process reagent and combination of the process reagent with the homogenized sample or the consumable sample. For instance, the process reagent can be delivered from a module integrated with one or more portions of the driving element 120 (e.g., from the plunger 128, from beneath the grinder 122), such that the process reagent does not originate from within the second chamber 130. As such, mixing of the consumable sample with a process reagent can occur prior to grinding of the consumable sample by a driving element 120.

The process reagent preferably includes an extraction solution configured to extract at least one analyte, associated with a harmful substance, from the homogenized sample, that can be detected at a detection substrate and used to indicate presence of the harmful substance. In an example for gluten detection, the extraction solution can contain 2-mercaptoethanol, or tris(2-carboxyethyl)phosphine, which operates by reducing disulfide prolamin crosslinking in a sample, and solubilizes proteins in the sample to facilitate detection. The extraction solution can additionally or alternatively contain guanidine hydrochloride, or N-lauroylsarcosine, or other disaggregating agents. In variations for other allergens, the extraction solution can include ethanol for a dairy-derived allergen (e.g., lactose), a parvalbumin extraction solution for a fish-derived allergen, an ara-h2 extraction solution for a nut derived allergen, an egg protein extraction solution for an egg-derived allergen (e.g., ovomucoid protein, ovalbumin protein, ovotransferrin protein, lysozyme protein), a tropomyosin extraction solution for a shellfish-derived allergen, and/or any other suitable extraction solution for any other harmful substance. Furthermore, variations of the process reagent(s) can additionally or alternatively include any one or more of: a reagent for lysing of a sample, a reagent for solubilization of a sample, a reagent for buffering of a sample, a reagent for dilution of a sample, and any other suitable reagent(s). For instance, in some variations, extraction and dilution of a sample to generate a dispersion can involve a first process reagent for extraction (e.g., an alcohol-based solution for extraction of gluten), and a second process reagent for dilution of a sample processed with the first process reagent, such that the dispersion has appropriate characteristics for assessment at a detection substrate 150.

In variations, the second chamber 130 can be prepackaged (e.g., prior to receipt of a consumable sample through the consumable reception opening 112) with one or more mixing elements 134 (e.g., magnets, etc.), in order to facilitate mixing of processing reagent and the consumable sample upon receipt of the consumable sample in the second chamber 130. The one or more mixing elements 134 can be prepackaged with or separated from processing reagent and/or other suitable components. However, the second chamber can house any suitable components prior to, during, and/or after receipt of the consumable sample at any suitable component of the test container 105.

The outlet port 136 functions to facilitate delivery of a controlled volume (and/or rate of flow) of the dispersion, from the second chamber 130, to an analysis chamber 140 for detection of the harmful substance(s) within the consumable sample. The outlet port 136 is preferably situated at an inferior portion of the second chamber, an example of which is shown in FIG. 2B, in order to facilitate delivery of the dispersion from the second chamber at least in part by gravity. However, the outlet port 136 can alternatively be configured at any suitable location relative to the second chamber. The outlet port 136 preferably allows a volume of the dispersion to be transmitted to a detection substrate 150 at an analysis chamber 140 in communication with the port, wherein the volume of the dispersion is configured so as to provide an adequate amount of the dispersion without flooding the detection substrate. In a specific example, an outlet port 136 of the second chamber 130 can be sized to be impermeable to residual particles resulting from the breaking of a frangible region 161 of the diaphragm 160 when the diaphragm is detachably coupled to the interior wall of the test container body. However, the outlet port can have any suitable dimensions.

Figures 6A, 6B:
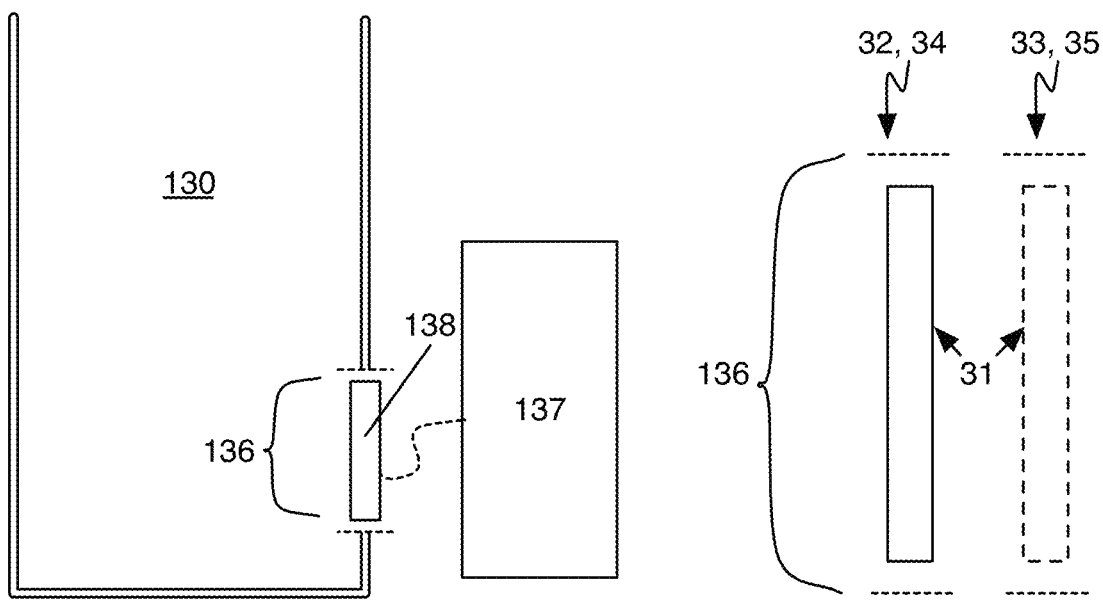
FIGS. 6A and 6B depict variations of a valve mechanism in an embodiment of a system for detection of harmful substances.
Figure 22:
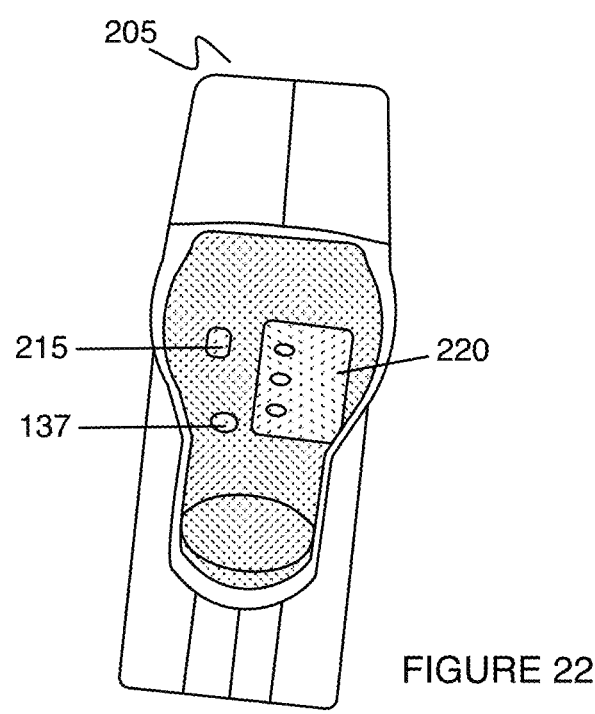
FIG. 22 depicts a variation of an analysis module for detection of harmful substances.

While the outlet port 136 can be configured to passively facilitate delivery of the dispersion to a detection substrate at the analysis chamber 140, variations of the system 100, as shown in FIGS. 6A and 22, can include an actuation system 137 configured to provide or meter a controlled volume of the dispersion to the analysis chamber 140. In one variation, an actuation system 137 coupled to the outlet port 136 can include a valve 138 that can be controllably opened and/or closed in order to dispense the dispersion into the analysis chamber 140 with a controlled volume and/or at a controlled time point. In an example, the valve 138 can include a rod 31 (e.g., needle) that is biased to be closed in a first valve configuration 32 and configured to open in a second valve configuration 33, wherein transitioning between the first valve configuration 32 and the second valve configuration 33 can be controlled by actuators (e.g., solenoids, etc.) of the test container 105 and/or analysis device 205, pressurization of the test container 105 (e.g., using a pneumatic mechanism), and/or in any other suitable manner. In the example, the rod can be biased closed using a compression spring (or other elastomeric element), and configured to transition between the first valve configuration 32 and the second valve configuration 33 upon user input (e.g., by pushing a button on the test container or the analysis device, by inputting a command at a user interface, etc.) and/or automatically (e.g., controlled by a controller of the system 100).

In another example, the outlet port 136 can include a material valve 138 configured to transition from a first state 34 to a second state 35 (e.g., reversibly, irreversibly), thereby allowing a volume of the dispersion to pass through the outlet port 136 in a controlled manner. In variations of this example, the material of the valve 138 can include any one or more of: a material (e.g., salt, sugar, polyvinyl alcohol, etc.) configured to transition from a solid state to a dissolved state (e.g., dissolvable salt wall, dissolvable in a manner that does not affect detection of an analyte at the detection substrate), a wax configured to transition from a solid state to a melted state, a material (e.g., foil, metals, plastics, etc.) configured to transition from an unpunctured state to a punctured state, and/or any other material configured to transition between states without affecting test results (e.g., without interfering with the delivery of a volume of a dispersion to a detection substrate, etc.). The transition between a first material valve configuration (e.g., closed) to a second material valve configuration (e.g., open, facilitating delivery of a volume of the dispersion) is preferably controlled by a component (e.g., a mechanical actuator, a heating element, a fluid dispersion module dispersing fluid for dissolving the material valve, etc.) of the analysis device 205. In a specific example, the analysis device 205 can include a valve motor coupled to a valve plunger that manipulates a rake to pierce a seal of the outlet port 136 in order to open the valve hole and transition the outlet port from a first to a second configuration. However, valve-controlling components of the analysis device 205 can apply any suitable force, movement, and/or action in opening and/or closing pathways through the outlet port 136. However, the transition from the first to the second valve configuration can also be controlled by components of the test container 105, actions by the user, and/or any through any other suitable mechanism.

In another example, the outlet port 136 can be characterized by varying levels of permeability to the consumable sample, homogenized sample, liquid dispersion, components of the test container 105 (e.g., diaphragm 160, residual pieces from a broken frangible region of the diaphragm 160, etc.), and/or other suitable materials of the test container top 106 and/or sample, depending on the configuration state (e.g., between an open and a closed configuration) of the outlet port 136. In a specific example where the second chamber 130 includes an outlet port 136 including a valve 138, the analysis device 205 can include a valve motor that controls the valve 138 of the outlet port 136 to operate between: a closed position where the outlet port 136 is impermeable to flow of the consumable sample through the outlet port 136, and an open position wherein the outlet port 136 is permeable to the flow of the consumable sample through the outlet port 136, and impermeable to movement of the magnetic diaphragm 160' through the outlet port 136. In specific examples, the outlet port can include flow passage features to enable and or prevent flow of sample and/or other components. The outlet port can define protrusions, standoffs, biofilms, fluid blocking agents, damming agents, features affecting fluid dynamics, standoffs, and/or any other suitable features affecting sample flow through the outlet port 136. In an illustration, the outlet port 136 can include a flow regulator (e.g., a foam dam) to regulate the flow of the dispersion and/or other suitable component to the detection substrate 150. The flow regulator is preferably arranged at an interface between the outlet port 136 and the detection substrate 150, but can be otherwise positioned in relation to the outlet port 136. The flow regulator can preferably retain a specific volume of the dispersion and/or facilitate the delivery of a specific volume of the dispersion to the analysis chamber 140. However, the outlet port 136 can possess and/or be defined by any suitable flow passage characteristics.

Figure 20:
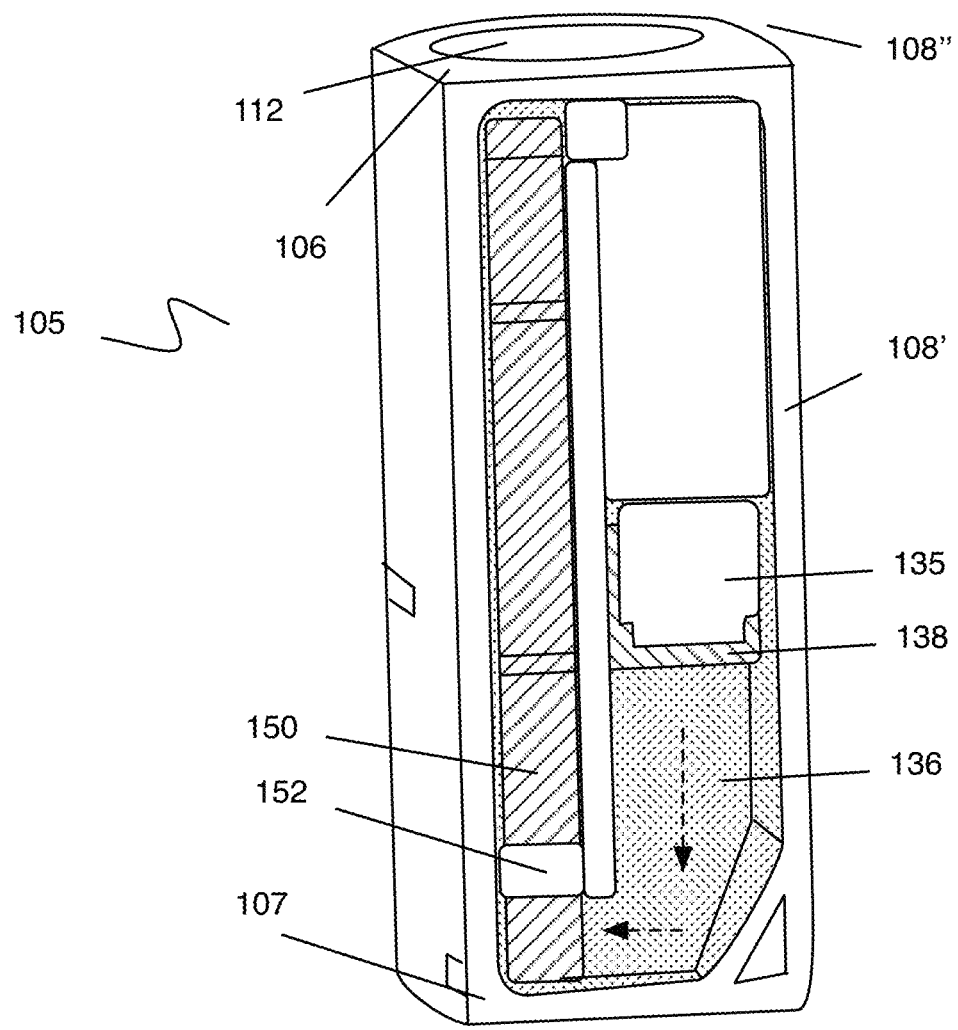
FIG. 20 depicts a variation of a system for detection of harmful substances.

In another example, the outlet port 136 can define (e.g., along with a first chamber 110, a second chamber 130, an analysis chamber 140, etc.) a sample fluid path through which a consumable sample would travel during operation of the test container 105 with the analysis device 205 in the alignment configuration 211. The outlet port 136 can be appropriately dimensioned to define a specific fluid path. As shown in FIG. 20, for example, the outlet port 136, can be defined by test container body interior walls that are straight, angled, curved, and/or with any suitable orientation to define a corresponding sample fluid path. In a specific example, the outlet port 136 of the second chamber 110 can define a sample fluid path extending along a lateral axis of the test container body, but can otherwise define sample fluid paths along any suitable reference feature (e.g., any suitable axis, plane, angle, etc.) of the test container body. In specific examples, the outlet port 136 can define microfluidic pathways configured to transfer the consumable sample from the second chamber 130 to one or more suitable components (e.g., an analysis chamber 140, a chamber for further processing, etc.). However, the outlet port can be otherwise configured for defining a sample fluid path.

In another example, the outlet port 136 can be appropriately dimensioned (e.g., based upon the viscosity of the dispersion) to allow the controlled volume of the dispersion to pass into the analysis chamber 140. In variations of this example, positive pressure and/or negative pressure can also be used to drive the dispersion out of the port and into the analysis chamber.

In still another example, the outlet port 136 can include a valve 138 (e.g., a membrane, a film) that can be punctured or otherwise compromised to allow a volume of the dispersion to pass through the outlet port 136 and into the analysis chamber 140. In this example, the valve 138 could be compromised using a needle coupled to a portion of the second chamber, wherein the needle could be deflected (e.g., by a portion of the analysis device 205, in combination with spring-loading of the needle) in a manner that prevents accidental deflection by a user or other entity in contact with the test container 105. As such, the actuation system 137 can operate as a release mechanism that allows the dispersion to be conducted to a detection substrate at the analysis chamber 140. The outlet port 136 and/or actuation system 137 can, however, be configured in any other suitable manner and/or include any other suitable elements that enhance detection at a detection substrate. For instance, one variation of the outlet port 136 can include a filter proximal the port that prevents material (e.g., material that could adversely affect detection) from passing into the analysis chamber 140 and/or from reaching the detection substrate 150.

However, the second chamber 130 and/or components of the second chamber 130 can be configured in any suitable manner.

3.1.D Test Container—Diaphragm

Figure 7:
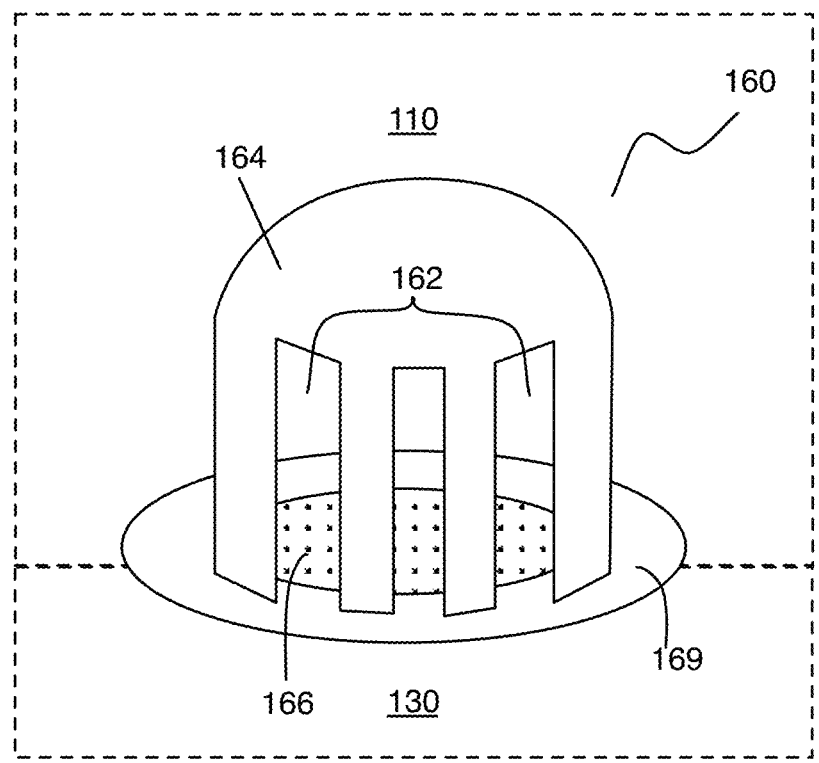
FIGS. 7 and 8 depict variations and configurations of a portion of a system for detection of harmful substances.
Figure 8:
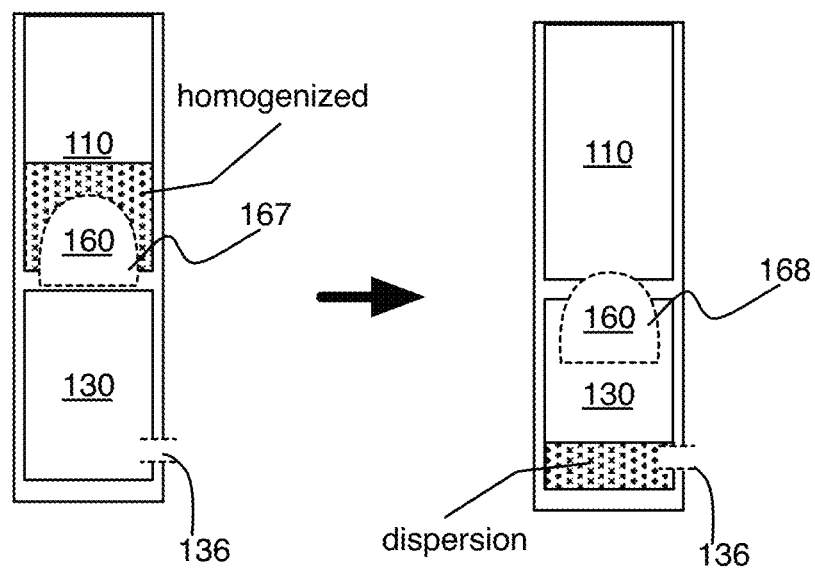

In some embodiments, as shown in FIGS. 2A, 2B, and 7, the system 100 can include a diaphragm 160 situated between the first chamber 110 and the second chamber 130, which functions to facilitate delivery of the homogenized sample, after processing of the consumable sample, into the second chamber 130 in a controlled manner. In one variation, the diaphragm 160 can obstruct flow of the consumable sample from the first chamber 110 to the second chamber 130 through the second opening 114 (e.g., defined by the first chamber 110) and a sample reception opening 132 (e.g., defined by the second chamber 130). In this variation, the diaphragm 160 can extend across the second opening, the sample reception opening, the fluid manifold cross section, or across any other suitable fluid path. In a second variation, the diaphragm 160 can extend across a cross section of the test container chamber and segment the test container chamber into the first chamber and the second chamber. However, the diaphragm 160 can be arranged at any suitable location relative the first chamber 110 (e.g., located substantially and/or completely within the first chamber 110), the second chamber 130 (e.g., located substantially and/or completely within the second chamber 130), and/or any suitable component of the test container 105.

In one variation, the diaphragm 160 can include a set of openings 162 configured to allow passage of homogenized portions of the consumable sample, during processing, into a cavity formed by the diaphragm. In this variation, the diaphragm can further include a roof 164 at a superior portion of the diaphragm 160, wherein the roof 164 prevents passage of unprocessed portions of the consumable sample into the second chamber 130. In examples of this variation, the diaphragm has a height between 3 and 15 mm (e.g., 8 mm), in order to facilitate processing and transmission of a desired volume of the homogenized sample.

In variations, the set of openings 162 of the diaphragm 160 is preferably distributed uniformly about the second opening 114 of the first chamber 110 and/or the sample reception opening 132 of the second chamber 130, in order to facilitate reception of homogenized portions of the consumable sample into the diaphragm 160. However, the set of openings 162 can alternatively be arranged in any other suitable manner. The set of openings can be located at lateral surfaces (e.g., vertical surfaces) of the diaphragm 160, in the orientation of the diaphragm 160 shown in FIG. 7, and can additionally or alternatively be located at any other suitable surface of the diaphragm 160. Openings of the set of openings 162 are preferably rectangular in shape; however, the set of openings 162 can alternatively include openings that are any one or more of: polygonal, ellipsoidal, circular, and any other suitable shape. In variations, the set of openings 162 include rectangular openings that are from 2 mm to 15 mm in height (e.g., 7 mm in height) and 0.5 to 5 mm in width (e.g., 3 mm in width); however, other variations of the set of openings 164 can alternatively have any other suitable dimensions. Furthermore, the set of openings 162 can include non-identical openings (e.g., in shape, in dimensions, etc.) in other variations of the diaphragm 160.

The roof 164 of the diaphragm 160 is preferably non-planar (e.g., non-horizontally planar, in the orientation shown in FIGS. 2A and 7), and defines a concave surface facing the sample reception opening 132 of the second chamber 130, which promotes sliding of homogenized portions of the consumable sample off of the roof 164 and toward openings of the set of openings 162 of the diaphragm. The concave surface can be blunt or sharp, and in examples, can include a semi-spherical surface, a semi-conical surface, a semi-pyramidal surface, a prismatic surface, and/or any other suitable surface. Alternatively, the roof 164 of the diaphragm 160 can include a planar surface, or a non-concave surface.

Figure 24:
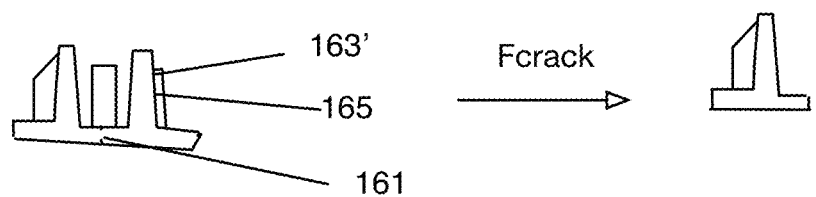

The diaphragm 160 can house one or more magnetic elements (e.g., one or more magnets, reagent (e.g., mixing reagent, processing reagent), actuating elements, force-applying elements (e.g., a mixing motor, etc.), and/or any suitable components. In a specific example, as shown in FIG. 18, the diaphragm 160 can include a set of magnetic elements 163', 163", embedded in a magnetic diaphragm 160', situated between the first and second chambers. Elements (e.g., magnetic elements) of the diaphragm 160 can possess any suitable shape, including one or more of a: bar, cross, sphere (e.g., ball bearing), and/or any other suitable shape or combination of shapes. Alternatively, the diaphragm itself can be made of magnetic material (e.g., ferrous material). Alternatively, the diaphragm can reversibly house the magnetic elements. In one example, driving element coupling and torsion along a keying interface defined in the diaphragm can open a door that releases the magnetic element(s). However, the magnetic elements can be otherwise supported by the diaphragm. The magnetic element can be arranged along an inferior surface of the diaphragm (e.g., surface proximal the second chamber), a superior surface of the diaphragm (e.g., surface proximal the first chamber), embedded within the diaphragm thickness, or otherwise arranged. In a specific example (shown in FIG. 24), the grinding elements of the diaphragm can be magnetic, wherein the grinding elements also function as the magnetic elements in the second configuration (e.g., mixing mode). However, the diaphragm 160 can house, include, and/or be embedded with any suitable components possessing any suitable shape. When the diaphragm includes multiple magnetic elements, the multiple magnetic elements can have the same polarity or different polarities. Alternatively, each magnetic element can include a north and south pole. However, the magnetic elements can be otherwise configured.

The diaphragm 160 can include one or more diaphragm grinding features 165. The one or more diaphragm grinding features 165 preferably extend away from a broad face defined by the diaphragm 160 (grinding face). The grinding face can: be proximal the first chamber, define the first chamber, be defined by the first chamber, proximal the second chamber, define the second chamber, be defined by the second chamber, or be otherwise defined. Additionally or alternatively, the one or more diaphragm grinding features 165 can be physically connected to an opposing broad face proximal the second chamber 130, where the diaphragm grinding features 165 can further facilitate homogenization of the consumable sample in the second chamber 130 (e.g., contemporaneously with mixing the consumable sample with processing reagent in the second chamber 130). However, the diaphragm 160 can include diaphragm grinding features 165 arranged at any suitable location along the diaphragm 160. The diaphragm grinding features 165 are preferably shorter than the length of the first chamber, but can alternatively be longer or substantially equal in length. The diaphragm grinding features 165 can include one or more fins, protrusions, plungers, sharp edges, dull edges, and/or any suitable feature for mechanical processing of the consumable sample. In examples, the diaphragm grinding features 165 can have magnetic properties (e.g., be constructed with magnetic material), include one or more magnetic elements 163, and/or have any suitable relationship with magnetic elements 163.

Figure 23:
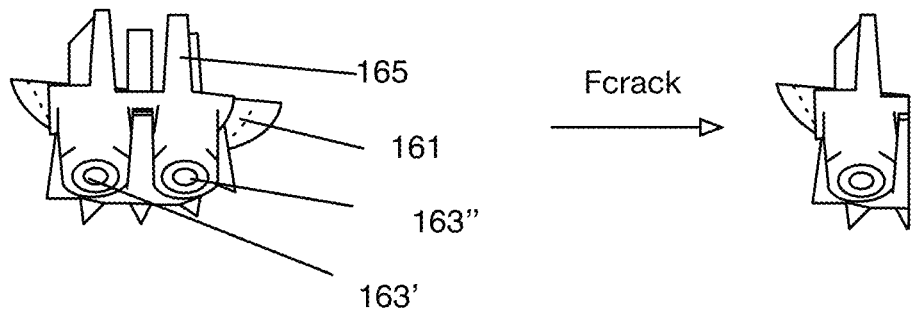
FIGS. 23-25 are schematic representations of a first, second, and third example of the magnetic diaphragm transitioning from the cohesive configuration to the broken configuration.
Figure 25:
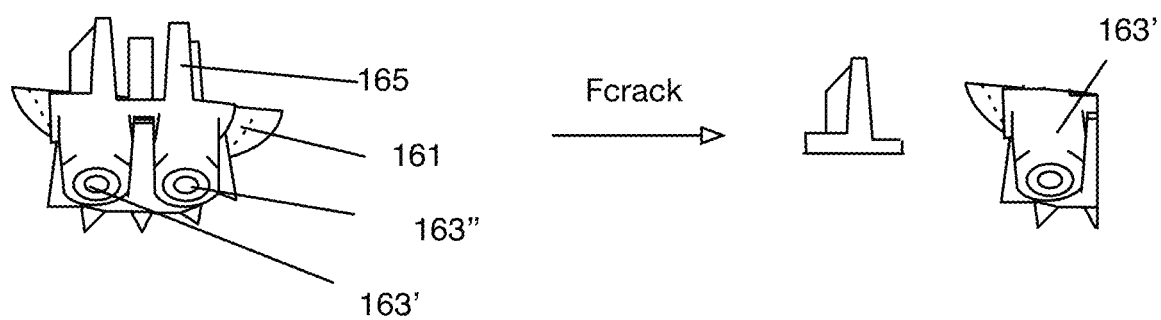

The diaphragm 160 is preferably at least partially constructed with frangible materials or configurations (e.g., used for a frangible region 161 of the diaphragm 160), thereby enabling destruction of the coupling mechanism between the diaphragm 160 and an interior wall of the test container body (e.g., an interior wall of the first chamber 110, an interior wall of the second chamber 130, etc.), leading to operation of the diaphragm 160 in a mixing mode for mixing the consumable sample with processing reagent in the second chamber 130. Additionally or alternatively the diaphragm 160 can be constructed using degradable materials, non-degradable materials, glass, metal, ceramic, plastic, or any other suitable material or combination thereof. The frangible region 161 can be defined by: frangible material (e.g., brittle material, such as ceramic), a thinned portion (e.g., with less than a threshold thickness, such as 1 mm), a perforated portion (e.g., wherein holes are periodically drilled along the frangible region), or be otherwise defined. The frangible region 161 can extend: along an arcuate region arranged radially inward of the diaphragm perimeter (e.g., as shown in FIG. 19), along the diaphragm perimeter, along a chord of the diaphragm, along a radius of the diaphragm, along a diameter of the diaphragm, or along any other suitable location. The frangible region(s) can be arranged between adjacent magnetic elements (example shown in FIG. 23), arranged between diaphragm grinding features 165 (example shown in FIG. 24), arranged between a magnetic element 163 and a diaphragm grinding feature 165 (example shown in FIG. 25), or be otherwise arranged relative to multiple magnetic elements.

The frangible region is preferably configured to break (and transition the diaphragm 160 from a first configuration (e.g., a retention mode impeding flow of the consumable sample from the first chamber 110 to the second chamber 130) to a second configuration (e.g., a mixing mode where the diaphragm 160 acts as a mixing element 134 in the second chamber 130). In an example, the frangible region 161 is preferably constructed with frangible materials facilitating a clean break (e.g., with few residual particles) of the frangible region 161, such that the consumable sample is not mixed with residual particles of the frangible region 161 of the diaphragm 160 when the consumable sample is mixed in the second chamber 130. Alternatively, the frangible region 161 can be otherwise configured to minimize interference with downstream processing and analysis (e.g., in a second chamber 130, in an analysis chamber 140, etc.) of the consumable sample. However, the frangible region 161 can be configured in any suitable manner.

Alternatively, the diaphragm can be removably coupled to the test container by the diaphragm perimeter, wherein the diaphragm is threaded down to the last thread within the first chamber. The diaphragm is preferably twisted by the driving element and falls off the last thread when the driving element (e.g., cap) is screwed down or forced down into the first chamber. However, the diaphragm can be otherwise removably coupled to the test container.

In another example, the processing reagent can be delivered from a diaphragm 160 (e.g., processing reagent housed within a magnetic diaphragm including one or more magnetic elements and one or more processing reagents). Delivery from a diaphragm 160 can be through one or more of: holes in the diaphragm 160, degradation and/or breakage of the diaphragm 160 (and/or reservoir or pouch on the diaphragm), and/or any other suitable mechanism. However, the process reagent and/or any other suitable solution can be delivered to the second chamber 130 and/or other component of the system 100 in any suitable manner.

The diaphragm 160 preferably has a first configuration 167 that retains at least a portion of the homogenized sample within the diaphragm 160 and a second configuration 168 that facilitates delivery of the homogenized sample into the sample reception opening 132 of the second chamber 130. In relation to the plunger 128 of the driving element 120 described above, the plunger 128 can be configured to be depressed or otherwise moved in any other suitable fashion in order to transition the diaphragm 160 between the first configuration 167 and the second configuration 168. In a first variation, the first configuration 167 is a raised configuration wherein a majority of the diaphragm 160 is situated within the first chamber 110, and openings of the diaphragm 160 are accessible from within the first chamber 110. In the first variation, the second configuration 167 is a depressed configuration wherein a majority of the diaphragm 160 is situated within the second chamber 130, and openings of the diaphragm 160 are substantially inaccessible from within the first chamber 110 (but open to the second chamber 130). In this variation, the diaphragm 160 can include at least one lip 169 circumscribing a portion of the diaphragm, wherein the lip 169 functions as a stop that constrains a range of motion of the diaphragm 160 between the first configuration 167 and/or the second configuration 168. Variations of the diaphragm 160 can, however, omit a lip 169. For instance, in variations wherein the diaphragm 160 can function as a mixing element 134, as described above, the diaphragm 160 can be configured to enter the second chamber 130 (e.g., drop entirely into the second chamber 130), and function as a mixing element that complements a mixing module of an analysis device 205. In a second variation, the first configuration 167 of the diaphragm 160 is an undeformed configuration, wherein a majority of the diaphragm 160 is situated within the first chamber 110, and openings of the diaphragm 160 are accessible from within the first chamber 110. In the second variation, the second configuration is a deformed configuration whereby at least one portion (e.g., the roof 164) of the diaphragm 160 is deformed to drive homogenized portions of the consumable sample from an interior portion of the diaphragm 160 and into the second chamber 130. In any of these variations, the diaphragm can be configured to be reversibly transitioned between the first configuration 167 and the second configuration 168; however, the diaphragm 160 can alternatively be configured to not be reversibly transitioned between the first configuration 167 and the second configuration 168.

In a third variation, the diaphragm 160 is assembled in the first configuration 167 through injection molding of the diaphragm with the test container at interior walls of the first chamber 110 (e.g., interior walls defining the second opening 114 of the first chamber 110) and/or interior walls of the second chamber 130 (e.g., interior walls defining the sample reception opening 132). The injection molding preferably creates a weak physical coupling between the diaphragm 160 and the interior walls of the first chamber 110 and/or second chamber 130 (e.g., the frangible region 161). In providing weak coupling, by way of an injection molding process, completion of twisting of the driving element 120 (e.g., test container cap) of the test container 105 can result in a component (e.g., grinder 122, shearing protrusion 124, etc.) of the driving element 120 applying a temporary force (e.g., cracking force) to the diaphragm 160 (e.g., to the frangible region 161), thereby breaking coupling between the diaphragm 160 and an interior wall of the test container 105, to cause the diaphragm 160 to be released into the second chamber 130.

In the fourth variation, destruction of the frangible region 161 is preferably facilitated by an applied force of a grinder 122 (e.g., a plunger 128 of the grinder 122, a shearing protrusion 124" of the grinder 122, etc.) of the driving element 120 physically interacting with the frangible region 161. Additionally or alternatively, the frangible region 161 can break through one or more of: dissolution (e.g., a dissolvable frangible region 161), melting, mechanical force applied by a component (e.g., a component of the analysis device 205, a component of the test container 105) other than the driving element 120 (e.g., a shear force, an axial force, etc.), and/or through any other suitable mechanism enabling the breakaway of the diaphragm 160. In an example of the fifth variation where the diaphragm 160 is a magnetic diaphragm 160', breakaway of the magnetic diaphragm 160' can be facilitated by magnetic attraction between magnetic elements 163 of the magnetic diaphragm and complementary magnets (e.g., of the mixing module 230). In another example of the fifth variation, the frangible region is at least partially destructed by an actuating element of the analysis device 205, the actuating element configured to apply a mechanical force to the frangible region 161 when the test container 105 and the analysis device 205 are in an alignment configuration 211. However, the test container 105 and/or analysis device 205 can include any suitable structural elements configured to facilitate destruction of one or more frangible regions 161 of one or more diaphragms 160.

In a fifth variation, the test container 105 includes one or more magnetic diaphragms 160. A magnetic diaphragm 160' can include one or more magnetic elements 163, can be constructed with magnetic materials, and/or include any suitable components conferring magnetic properties to the magnetic diaphragm 160'. Magnetic elements 163 of a magnetic diaphragm 160' can be embedded in the magnetic diaphragm 160', and/or positioned at any suitable location of the magnetic diaphragm 160'. The magnetic diaphragm 160' preferably possesses magnetic properties in a first configuration (e.g., a retention mode obstructing consumable sample flow) and in a second configuration (e.g., a mixing mode where the magnetic diaphragm acts as a mixing element in magnetically-driven mixing of the consumable sample in the second chamber 130), but can possess magnetic properties in any suitable configuration.

In examples of the fifth variation, one or more magnetic elements 163 are magnetically coupleable with a complementary magnet of a mixing module 230 of an analysis device 205. Magnetic coupling with the complementary magnet preferably facilitates mixing of the homogenized sample with processing reagent housed in the second chamber 130. Additionally or alternatively, the one or more magnetic elements 163 can be magnetically coupleable with any suitable magnet of the system 100. In these examples, interior walls of the second chamber can define mixing features configured to facilitate magnetic coupling between a magnetic element 163 and a complementary magnet. For example, an interior wall of the second chamber 130 can define indentations (e.g., concave dimples) geometrically complementary to a magnetic element 163 and/or a portion of the diaphragm housing a magnetic element 163. However, the second chamber 130 and/or components of the test container 105 can include any suitable features facilitating magnetic coupling of magnetic elements of the system 100.

The diaphragm 160 can additionally or alternatively include a temporary obstruction region 166, opposite the roof 164, that retains at least a portion of the homogenized sample within the diaphragm 160. Retention of the portion of the homogenized sample can be performed by the temporary obstruction region 166 in the first configuration 168 of the diaphragm 160, and/or in any other suitable configuration of the diaphragm 160. In one example, the temporary obstruction region 166 can include a dissolvable membrane configured to dissolve and release the homogenized sample into the second chamber 130 after a desired condition (e.g., a condition involving a threshold volume of the homogenized sample within the diaphragm) has been met. In another example, the temporary obstruction region 166 can include a screen (e.g., a mesh screen, a filter) configured to further facilitate processing of the consumable sample/homogenized sample to have a desired particle dimension prior to transmission into the second chamber 130. The temporary obstruction region 166 can, however, include any other suitable materials and/or be configured in any other suitable manner.

In relation to the test container chambers, including one or more of a first chamber 110 (e.g., grinding chamber), a second chamber 130 (e.g., mixing chamber), and/or an analysis chamber 140, one or more pressure stabilization holes can be defined at interface regions between two or more chambers. For example, the diaphragm 160 can include one or more pressure stabilization holes (e.g., extending through the thickness of the diaphragm 160). The pressure stabilization holes preferably stabilize the pressure differences between chambers of the test container in order to facilitate the flow (e.g., gravitational flow) of volumes within and between chambers. However, the flow of volumes between chambers of the system 100 can be facilitated in any other suitable manner.

While a first chamber 110 and a second chamber 130 are described above, in some variations, the test container 105 can include a single chamber configured to perform the functions of the first chamber 110 and the second chamber 130. For instance, in one variation, the first chamber 110 and the second chamber 130 can be physically contiguous as a single chamber can be used to receive a consumable sample, and to facilitate grinding and mixing of the consumable sample with one or more process reagents to extract and/or dilute a test sample for delivery to a detection substrate 150 for analysis. As such, the first chamber 110 and the second chamber 130 can be distinct from each other, or otherwise integrated into a single chamber that facilitates all sample processing performed using the system 100.

3.1.E Test Container—Analysis Chamber

The analysis chamber 140 functions to position a detection substrate 150 proximal the outlet port 136 of the second chamber, such that the detection substrate 150 can absorb a volume of the dispersion and provide indication of presence of at least one harmful substance within the consumable sample. The analysis chamber 140 is preferably coupled to at least one of the second chamber 130 and the first chamber, and in one variation, the analysis chamber 140 is configured external to the second chamber 130, with access between the second chamber 130 and the analysis chamber 140 provided by the outlet port 136 of the second chamber 130. In an example of this variation, the analysis chamber 140 can include a slot longitudinally spanning a portion of the test container 105, as shown in FIG. 2B, wherein the slot is configured to position the detection substrate 150 proximal the outlet port 136. Portions of the analysis chamber 140 and/or components of the analysis chamber 140 (e.g., detection substrate 150 are preferably aligned, adjacent, and/or proximal along a lateral axis of the first chamber 110 and/or second chamber 130, but can be in any suitable configuration with any suitable component. However, the analysis chamber 140 can alternatively be configured in any other suitable manner.

The detection substrate 150 functions to indicate presence of an analyte, associated with a harmful substance, and in variations, can indicate presence based upon one or more of: a color change, fluorescence emission, infrared emission, magnetic response, electrical response, acoustic change, and any other suitable mechanism of indication. The detection substrate 150 is preferably a permeable substrate (e.g., test strip) that soaks up a portion of the dispersion and facilitates binding of one or more analytes in the dispersion with complementary antibodies (e.g., antibodies bound to cellulose nanobeads) at the detection substrate 150, to provide indication of presence of harmful substances associated with the analyte(s). The detection substrate 150 can include a single active region (e.g., a band, a line, a dot, etc.) for analyte binding, or a set of active regions for analyte binding. The active region(s) can include antibody cocktails for a single analyte associated with a harmful substance, a set of analytes associated with different harmful substances, and/or a control region configured provide a control readout (e.g., in order to enable determination of a baseline signal, in order to establish proper conductance of a test). For instance, in some variations of a detection substrate 150 with a set of active regions 151 for analyte binding, one active region can be used as a test region that is used to indicate an amount (e.g., concentration, volume, mass) of a harmful substance in a consumable sample, and another active region can be used as a control region that indicates that the test has been performed properly (i.e., such that data generated from the detection substrate 150 is reliable). The detection substrate 150 preferably includes a beginning region and an end region respectively defining the beginning and end portions of a sample fluid path through the detection substrate 150. In a specific example, the analysis chamber 140 can include a detection substrate 150 extending along a longitudinal axis of the test container body, the detection substrate 150 including a beginning region fluidly connected to the second chamber 130 through the outlet port 136 of the second chamber 130, and an end region proximal the consumable reception opening of the first chamber 110. However, the beginning and end regions of a detection substrate 150 can have any suitable positional relationship with other components of the test container 105.

In variations, a region of a detection substrate 150 can be configured to accommodate an analyte with a single binding site, or multiple binding sites (e.g., as in a sandwich assay having a first antibody that serves as a capture antibody, and a second antibody that serves as an analyte-specific antibody). However, the detection substrate 150 can additionally or alternatively include any other suitable liquid medium or sensor configured to indicate presence of a harmful substance within the consumable sample in any other suitable manner. In an example, the detection substrate 150 is a long, narrow, and flat strip of a fibrous material with regions (e.g., bands, lines, spots) of complementary antibodies to an analyte associated with a harmful substance, whereby capillary soaking of the detection substrate 150 distributes the dispersion across the detection substrate 150. In a version of the example for gluten testing, the detection substrate 150 includes a control band and a test band, having a distribution of a G12 antibody, bound to cellulose nanobeads, which is configured to bind to the 33-mer peptide of the alpha-gliadin molecule in gluten.

In a variation, the analysis chamber 140 can include a detection substrate 150 including microfluidic pathways, including channels on a patterned-paper, lab-on-a-disc, lab-on-a-chip, and/or any other suitable microfluidic devices facilitating detection of target substances in the consumable sample. Additionally or alternatively, the analysis chamber 140 and/or detection substrate 150 can include any suitable elements described in U.S. application Ser. No. 15/065,198, filed 9 Mar. 2016, which is herein incorporated in its entirety by this reference.

In some variations, the analysis chamber 140 can include a detection window 142 that enables detection of presence of a harmful substance at the detection substrate 150. As such, the detection substrate 150 can be configured to align with the detection window, such that indicators (e.g., one or more lines generated during binding of analyte at the detection substrate) can be observed through the detection window 142. The detection window 142 can substantially span an entirety of the detection substrate, or can alternatively be configured to provide observation of one or more regions of interest of a detection substrate 150. Furthermore, the detection window 142 can include an opening through the analysis chamber 140, and can additionally or alternatively include a covering (e.g., transparent covering, translucent covering) that enables observation of the detection substrate 150. In variations, the detection window 142 can further function to indicate potential defectiveness of a test container 105, detection substrate 150, and/or any other suitable portion of the system 100 in providing reliable results. For instance, in some variations, wherein detection substrates are sensitive to heat and/or humidity, the detection window 142 can be configured to indicate subjection of a detection substrate 150 to high temperatures (e.g., above 40° C.) and/or humid environments (e.g., by producing a color change in the detection window, by having the detection window fog up, etc.). Additionally or alternatively, the test container 105 can be coupled with a dessicant to prevent humidity-induced damage, and furthermore, variations of the detection window 142 can additionally or alternatively provide any other suitable function that provides information regarding potential defectiveness of a test performed using the detection substrate 150, defectiveness in analyte detection, and/or any other suitable function. For instance, the detection window 142 can provide optical qualities that provide desired properties upon illumination in order to enhance analysis of a detection substrate 150. Variations of the analysis chamber 140 can, however, entirely omit the detection window 142. For instance, a variation of the system 100 can be configured such that the detection substrate is retrieved after contacting a volume of the dispersion, and analyzed away from an analysis chamber 140 of a test container 105.

In variations with a detection window 142, the detection window 142 preferably constructed with materials and or sealants preventing liquid (e.g., dispersion, consumable sample, etc.) from unintentionally leaking from the test container 105 (e.g., onto other components of the test container 105, onto the analysis device 205). The detection window 142 is preferably coupled to the remaining test container 105 with a sealant (e.g., heat seal), but can additionally or alternatively be coupled to the test container through adhesives (e.g., UV glue), press fitting (e.g., ultrasonic), and/or any other suitable mechanism. The detection window 142 is preferably made of a rigid material (e.g., brittle plastic, plastic blend, etc.) that prevents a user from piercing the detection window 142. Additionally or alternatively, the detection window 142 can be made of a softer material and/or any other material possessing any suitable characteristic. In providing modularity, the detection window 142 can be made of multiple components and/or materials. For example, the detection window 142 can include a rigid component to prevent user penetration and a softer component to facilitate penetration by the valve plunger. However, the detection window can be assembled with any suitable materials and/or sealants.

3.1.F Test Container—Motor Cavity

Figure 21:
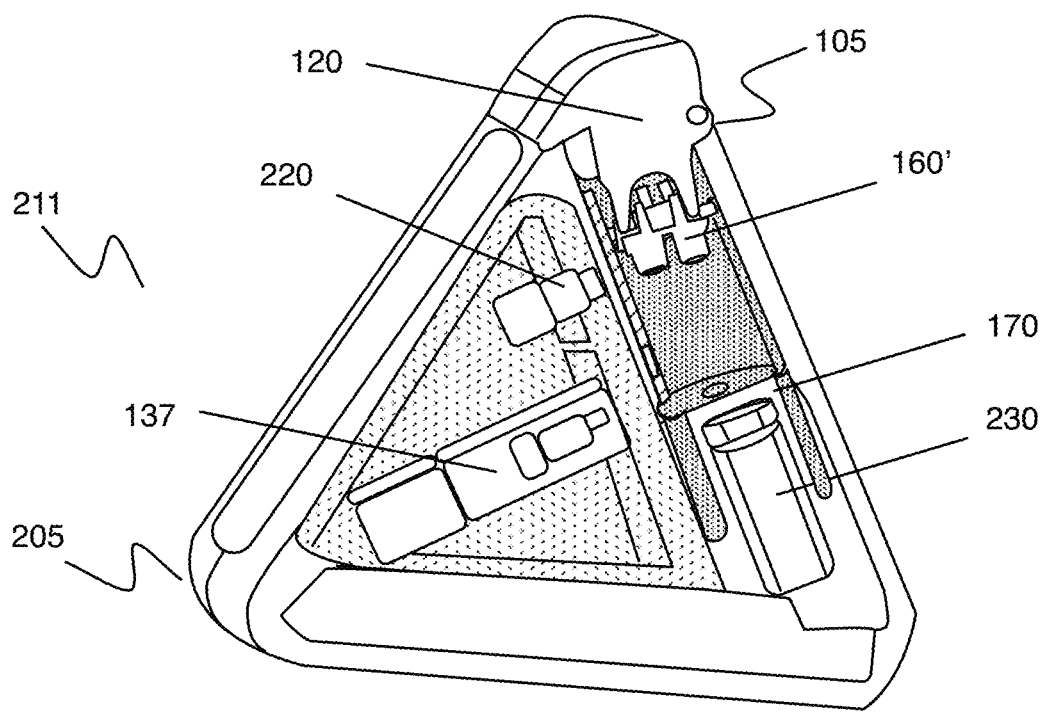
FIG. 21 depicts a variation of an analysis module for detection of harmful substances.

As shown in FIGS. 18 and 21, the test container 105 can additionally or alternatively include a motor cavity 170, which functions to align the test container 105 and the analysis device 205 (e.g., facilitate orientation in an alignment configuration 211). The motor cavity 170 can additionally or alternatively function to facilitate engagement of the mixing module 230 with test container components (e.g., magnetic elements 163). The motor cavity 170 is preferably proximal the test container bottom 107, and is preferably aligned with the first and second chambers 110, 130 along a longitudinal axis of the test container 105. However, the motor cavity 170 can have any suitable positional relationship with components of the test container 105 and/or analysis device 205. Further, the motor cavity 170 preferably does not cooperatively define the sample fluid path, such that consumable sample and/or other fluid components (e.g., reagent) do not interface with the interior of the motor cavity 170, but the motor cavity 170 can alternatively define a portion of the sample fluid path (e.g., a motor cavity 170 additionally serving as a processing chamber). In the alignment configuration 211 between the test container 105 and the analysis device 205, the motor cavity 170 preferably substantially or fully encloses the mixing module 230 (e.g., a mixing motor and a complementary magnet), but can additionally or alternatively house any other suitable component (e.g., a valve motor for transitioning the outlet port 136 from a closed to an open configuration). In a specific example, the motor cavity 170 additionally or alternatively houses a sensor (e.g., a weight sensor, a light sensor, etc.) for measuring characteristics of the consumable sample in the second chamber 130. However, the motor cavity 170 can be configured in any suitable manner.

Variations of the test container 105, as noted earlier, can be characterized by modularity in using a combination of reusable and/or non-reusable components, such that portions of the test container 105 can be reused, and other portions of the test container 105 can be disposed after a limited number of uses. For instance, in some variations, all portions of the test container 105 can be configured to be reusable, aside from the detection substrate 150/analysis chamber 140, such that the detection substrate 150 are disposed after each use, and the test container 105 can be reused for another instance of detection upon replacement of the detection substrate 150/analysis chamber. In other variations, all portions of the test container 105 can be configured to be reusable, aside from the detection substrate 150, such that the detection substrate 150 are disposed after each use, and the test container 105 can be reused for another instance of detection upon replacement of the detection substrate 150. The test container 105 can, however, provide any other suitable combination of reusable and disposable components. In providing modularity, portions of the test container 105 are preferably made of a material that is recyclable, compostable and/or processable, and in variations, can include any one or more of: a polymer (e.g., a plastic), a metal, and a glass. For example, a portion of the test container 105 can be made of a compostable material, while the detection window 142 of the test container can be made of a recyclable plastic. However, variations of the test container 105 can alternatively include any other suitable material (e.g., ceramic), and can be configured to be entirely reusable or entirely disposable.

As a person skilled in the art will recognize from the previous detailed description and from the figures and claims, modifications and changes can be made to the embodiments of the test container 105 without departing from the scope of the test container 105.

3.1.G Test Container—Test Container Body

As shown in FIG. 20, the test container can additionally or alternatively include a test container body, which functions to provide mechanical support and/or shielding to components of the test container 105. The test container body can include a test container top 106, a test container bottom 107 opposing the test container top 106, and/or any suitable number of side walls 108 physically connecting the test container top 106 and the test container bottom 107. However, the test container body can include any suitable components in any suitable configuration.

As shown in FIG. 20, in a variation, the test container body can be keyed (e.g., possess an asymmetric profile) for insertion into the analysis device 205. For example, the test container 105 can include a curved side wall 108' and a flat side wall 108". In another example, the test container body can define a test container top geometrically asymmetric from a test container bottom. In a specific example, the test container body can define a curved side 108' physically connected to the test container top 106 and the test container bottom 107, wherein the curved side is proximal the first chamber 110 and the second chamber 130 of the test container 105. In this specific example, the test container body can additionally or alternatively define a flat side 108" opposing the curved side 108' and physically connected to the test container top 106 and the test container bottom 107, wherein the flat side 108" is proximal the analysis chamber. In a second example, the test container 105 can define a cross section including a tongue, complementary to a groove defined by the analysis device opening. However, the test container body can be configured in any suitable manner.

3.2 System—Analysis Device

As noted above and shown in FIG. 1, in an embodiment, the analysis device 205 includes: a receiving port 210 configured to receive the test container 105, a mixing module 230 configured to mix the homogenized sample with a process reagent, an optical sensing subsystem 220 configured to enable detection of presence of the harmful substance at the detection substrate 150, and a processing and control system 240 configured to receive and process signals from the optical sensing subsystem 220, thereby producing an output indicative of presence of the harmful substance in the consumable sample.

As shown in FIG. 16A, in variations, the analysis device 205 can include and/or define a base 206 and one or more triangular faces 207 physically connected to the base 206, the one or more triangular faces 207 defining an apex 208. In a specific example, the analysis device 205 can be characterized by a triangular prism form including a base 206 and two triangular faces 207 extending substantially normally from opposing sides of the base. The analysis device 205 can additionally or alternatively include side walls physically connected to the base 206 and physically connecting the one or more faces 207. The side walls can be flat, curved, and/or otherwise configured. However, the analysis device 205 and/or components of the analysis device 205 can be defined by any suitable geometric characteristics.

3.2.A Analysis Device—Receiving Port

The receiving port 210 functions to receive the test container 105, and can additionally function to align the test container 105 to facilitate detection of analytes at a detection substrate, in cooperation with the optical sensing subsystem 220. The receiving port 210 preferably defines a test container opening sized to receive the test container 105. As such, the receiving port 210 preferably mates with the test container 105 (e.g., an external morphology of the test container 105), in a consistent manner, such that the test container 105 can only be positioned within the receiving port 210 of the analysis device in one of a discrete set of orientations (e.g., in variations wherein the test container 105 has an orientation). In a specific example, the receiving port can be geometrically complementary to the test container 205, where the receiving port 210 can include a superior portion geometrically complementary to a test container top 106, and an inferior portion geometrically complementary to a test container bottom 107. Alternatively, in variations wherein the test container 105 is symmetric (e.g., having a rotational axis of symmetry), the receiving port 210 can be configured to accommodate symmetry in the test container 105 in relation to positioning the test container 105 relative to other elements of the analysis device 205 (e.g., the optical sensing subsystem 220, the mixing module, 230). While the receiving port 210 can receive a test container 105 into an interior portion of the analysis device 205, receiving port 210 can additionally or alternatively be configured to couple the test container 105 to an external portion of the analysis device 205. For instance, the receiving port 210 can include a mechanism (e.g., latch, slide, magnet) configured to couple the test container 105 to at least a portion of the exterior of the analysis device 205.

In variations where the analysis device 205 defines a base 206 and a triangular face 207, the test container opening of the receiving port 210 can be proximal an apex 208 of the triangular face 207. Further, a longitudinal axis of the receiving port 210 can be substantially parallel a side of the triangular face 207 and/or angled with respect to the base 206 (e.g., perpendicular the base). Additionally or alternatively, a lateral axis of the receiving port can intersect a plane of the base 206. In this variation, a test container 105 can preferably be placed at the test container opening proximal the apex 208, and the test container 105 can be guided (e.g., slid, gravitationally driven, with guiding rails, etc.) into an alignment configuration 211 with the analysis device 205. However, the receiving port 210 can be oriented in any suitable configuration with respect to the analysis device 205 and/or test container 105.

Figure 9D:
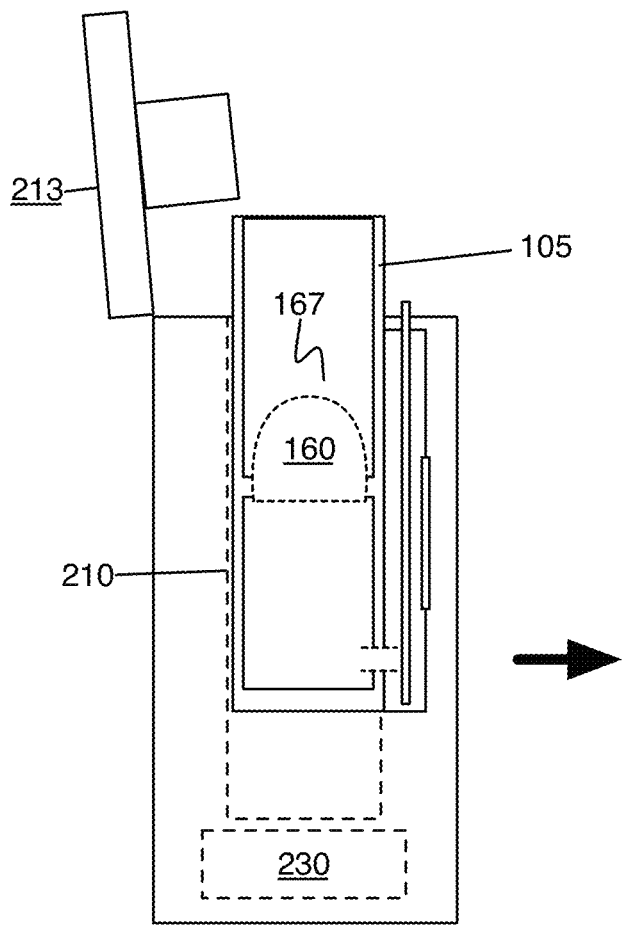
Figure 9E:
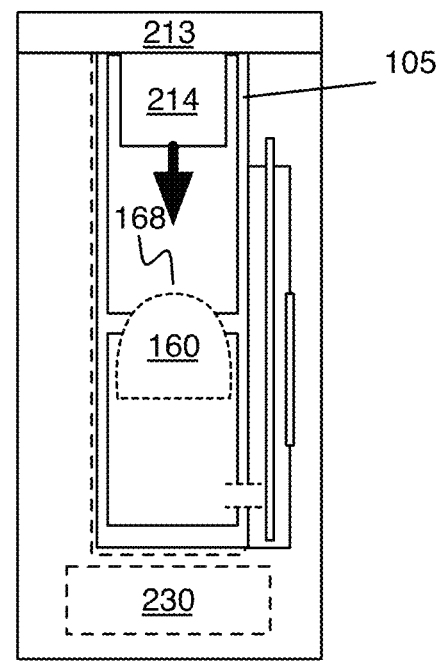

As such, in some variations, the receiving port 210 is preferably configured to receive the test container 105 in an alignment configuration 211, and to release the test container 105 from the analysis device 205 in a releasing configuration 212 (e.g., post-analysis of a sample), as shown in FIGS. 9A-9C. In producing the alignment configuration 211, the receiving port 210 can be coupled to a cap 213 or other mechanism (e.g., latch, tab, etc.) that facilitates retention (e.g., locking) of the test container 105 in the alignment configuration, thereby preventing undesired deviations from the alignment configuration, which could affect analysis of a detection substrate 150 of the test container 105. In variations of the receiving port 210 with a cap 213, the cap 213 can further function to facilitate processing of a consumable sample and/or homogenized sample within the test container. For instance, in one variation, the cap 213 can include an actuating element 214 (e.g., disposed within an interior surface of the cap 213, accessible from an exterior surface of the cap 213, etc.) configured to depress a plunger 128 of the test container 105 to transition a diaphragm between the first chamber 110 and the second chamber 130 of the test container 105 between a first configuration 167 and a second configuration 168, as shown in FIGS. 9D and 9E. The actuating element 214 can be magnetically driven, pneumatically driven, mechanically driven (e.g., using springs, etc.), or driven in any other suitable manner. Actuation of a plunger 128, as facilitated by the cap 213, in this variation can be automatically performed once the test container 105 is in the alignment configuration within the receiving port 210, and/or can be triggered (e.g., by the user, by a control system of the analysis device 205) in any other suitable manner. As such, in an example workflow of this variation, a user can place a test container 105 within the receiving port 210 of the analysis device, with the consumable sample substantially homogenized and the diaphragm 160 in the first configuration 167, and closing of the cap 213 can automatically initiate depressing of the plunger 128 to transition the diaphragm 160 into the second configuration 168 (e.g., without knowledge by the user). Then, after detection using the optical sensing subsystem 220, as described below, the cap 213 can be opened and the test container 105 can be released from the analysis device 205 in the releasing configuration. In variations, locking and unlocking of the test container 105 from the analysis device 205 can be manually triggered (e.g., by a user) through mechanical instructions (e.g., a button, switch), audio instructions (e.g., voice control, etc.), visual instructions (e.g., a hand gesture, etc.), touch instructions (e.g., tap, hold, pinch, touching of a digital user interface, pushing and/or pulling force applied to the test container 105 in the receiving port 210, etc.), and/or through any suitable mechanism. In other variations, locking and unlocking of the test container 105 can be automatically triggered, for example, at specific points along the sample fluid path (e.g., after detection of one or more analytes with the optical sensing subsystem 220, etc.), after detection of the test container 105 in the receiving port 210 (e.g., by a test container detection region 215 described below, etc.), and/or at any suitable time by any suitable mechanism. However, variations of the receiving port 210 can alternatively omit a cap or other mechanism configured to retain the test container 105 in the alignment configuration.

As shown in FIG. 22, in another variation, the receiving port 210 can include a test container detection region 215 configured to detect the receipt of the test container 105 at the receiving port 210 in an alignment configuration 211. The test container detection region 215 preferably includes a translucent region (e.g., constructed with glass, plastic, translucent materials, etc.) adjacent a sensor (e.g., a light sensor, a motion sensor, etc.) of the test container detection region 215. The sensor is preferably configured to determine whether a test container 105 is present in the receiving port 210 and/or whether the test container 105 is properly in an alignment configuration 211 with the analysis device 205. Additionally or alternatively, the test container detection region 215 can include any other suitable components facilitating detection of the test container top 105 at the analysis device 205.

However, the receiving port 210 and/or components of the receiving port 210 can be configured in any suitable fashion.

3.2.B Analysis Device—Mixing Module

The mixing module 230 functions to facilitate active mixing of a homogenized sample of the test container 105 with a process reagent (e.g., extraction reagent), in order to produce a dispersion that can be delivered to a detection substrate for analysis. The mixing module 230 preferably operates in cooperation with a mixing element 134 of the test container 105 (e.g., of a second chamber 130 of the test container), thereby forming a complementary portion of a mechanism that provides solution mixing. Thus, the mixing module 230 is preferably situated proximal to a portion of the test container 105 having the homogenized sample and the process reagent, in the alignment configuration of the test container 105. As shown in FIG. 21, when the test container 105 and analysis device 205 are in an alignment configuration 211, the mixing module 230 is preferably partially encapsulated by the motor cavity 170 of the test container 105, but can additionally or alternatively be positioned at any suitable location relative the test container 105 in the alignment configuration 211. As noted above and shown in FIG. 5, the mixing module 230 can provide a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example wherein the second chamber 130 of a test container 105 includes a magnetic mixing element 134, the mixing module 230 can include a complementary magnet situated proximal to the second chamber 130 in the alignment configuration of the system 100. In the example, the complementary magnet of the mixing module can be coupled to a spinning motor, thereby producing rotation at the magnetic mixing element 134 within the second chamber 130. In a specific example, the mixing module 230 can be proximal the base 206 of the analysis device 205, and wherein the mixing module 230 includes a complementary magnet coupleable to the magnetic element 163 of the magnetic diaphragm 160', and a spinning motor coupled to the complementary magnet. In variations of this example, the mixing module 230 can be configured to detect proper coupling between the complementary magnet of the mixing module 230 and the magnetic mixing element 134 within the second chamber 130 of the test container 105 (e.g., by way of sensing of a magnetic force, by way of detection of motion of the magnetic mixing element 134 in response to motion of the complementary magnet, etc.). The mixing module 230 can, however, be configured in any other suitable manner.

In a variation, the mixing module 230 can include a mixing status sensor configured to start and/or stop mixing based on a determined mixing status of the consumable sample in the second chamber 130. One or more mixing status sensors can include a light sensor, weight sensor, phase sensor (e.g., liquid, gaseous, solid phase), etc. Additionally or alternatively, mixing by the mixing module 230 can progress for a predetermined time period (e.g., determined by a manufacturer, by a user, etc.), an automatically determined time period (e.g., based on mixing status sensor readings), and/or for any suitable period of time.

In another variation, the mixing module 230 can include an actuation motor coupled to a complementary magnet of the mixing module 230, and configured to move the complementary magnet in response to completion of mixing in order to facilitate unimpeded flow of the liquid dispersion from the second chamber 130 through the outlet port 136. For example, after completion of mixing the consumable sample with processing reagent in the second chamber 130, an actuation motor of the mixing module 230 can move the complementary magnet (e.g., along a guided rail) to a position proximal a second chamber portion opposing the outlet port 136. However, the mixing module can facilitate consumable sample flow through the outlet port 136 in any suitable manner.

However, the mixing module 230 can be configured in any suitable fashion.

3.2.C Analysis Device—Optical Sensing Subsystem

As shown in FIG. 22, the optical sensing subsystem 220 functions to facilitate detection of one or more analytes, indicative of presence of a harmful substance within a consumable sample. The optical sensing subsystem 220 further functions to facilitate automated reading of a detection substrate 150, such that effects of user error are minimized; however, the optical sensing subsystem 220 can be configured to provide manual assessment of test results of a detection substrate 150. The optical sensing subsystem 220 is preferably aligned with the detection window 142 of the analysis chamber 140 of the test container 105 in the alignment configuration 211, as shown in FIG. 10, in order to provide a compact configuration and facilitate direct communication between a detection substrate and the optical sensing subsystem 220. In a specific example where the receiving port 210 defines a first side geometrically complementary to a curved side wall 108' of the test container body, and an optical analysis side opposing the first side and geometrically complementary to a flat side wall 108" of the test container body, the optical sensing subsystem 220 can be optically aligned with the optical analysis side of the receiving port 210. However, in other variations, the detection window 142 of the analysis chamber 140 and the optical sensing subsystem 220 can alternatively be misaligned, and configured to communicate using elements (e.g., mirrors, etc.) that facilitate indirect communication between a detection substrate 150 and the optical sensing subsystem 220. The optical sensing subsystem 220 preferably has an adequate sensitivity, resolution, and window of view in order to accurately and reliably detect signals from a detection substrate 150. In one variation, the sensitivity, resolution, and window of view cooperate to enable detection of a single analyte at a single region (e.g., dot, line, band) of a detection substrate 150 and in another variation, the sensitivity, resolution, and window of view cooperate to enable detection of multiple analytes (e.g., associated with different allergens) and/or control signals at multiple regions (e.g., dots, lines, bands) of a detection substrate 150. While one optical sensing subsystem 220 is described, the analysis device 205 can, however, include any other suitable number of optical sensors 220 to facilitate detection of one or more analytes at one or more regions of a detection substrate 150.

In a first variation, the optical sensing subsystem 220 can include a camera module 221 that is configured to image a detection substrate 150, through the detection window 142, and to generate a distribution (e.g., array) of pixel intensities corresponding to regions of the detection substrate. Then, in communication with the processing and control system 240 (described in further detail below), the distribution of pixel intensities generated from processing of a detection substrate 150 can be used to output a value of a parameter associated with an amount (e.g., concentration in parts per million, other concentration, mass, volume, etc.) of a harmful substance present in a consumable sample analyzed using the detection substrate 150. An example of pixel intensity distributions, prior to and post processing at the processing and control system 240, is shown in FIGS. 11A and 11B, respectively. The camera module 221 of the first variation preferably provides data within sufficient resolution to eliminate a requirement for tight coupling between the camera module 221 and a detection substrate 150; however, the camera module 221 can alternatively provide data with any other suitable resolution.

In the first variation, the camera module 221 can be provided along with an illumination module 222 configured to facilitate illumination of the detection substrate 150, in order to enable detection of the analyte(s) at the detection substrate. Illumination is preferably provided at an angle (e.g., an acute angle of incidence) relative to a surface of the detection window 142, in order to minimize reflection (e.g., from the detection window 142) that could interfere with sensing by the optical sensing subsystem 220. In specific examples, the illumination module can include one or more light-emitting diodes (LEDs) any/or any other suitable light sources. The LEDs/light sources can be configured to provide white light, or any suitable range of wavelengths of light. Furthermore, in variations wherein the illumination module 222 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. As such, illumination and or detection at an optical sensing subsystem 220 of the camera module 221 can be enabled in cooperation with one or more filters (e.g., wavelength filters, emission filters, excitation filters, etc.) configured to filter out any interfering signals.

Figure 12:
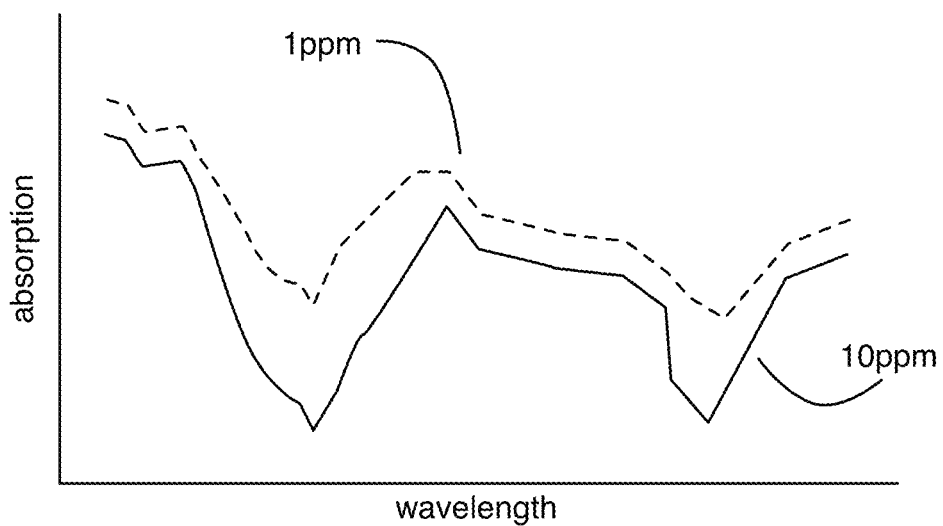
FIG. 12 depicts an example output of a system for detection of harmful substances.

In a second variation, the optical sensing subsystem 220 can include a photodiode system 223 that is configured to detect absorption and/or emission of light (e.g., wavelengths of light) indicative of presence of (i.e., an amount of) an analyte at a detection substrate in communication with the photodiode system 223. In one variation, the photodiode system 223 can include a photodiode configured to detect absorption of light associated with a peak absorption wavelength of an active region of a detection substrate (e.g., in order to assess absorption at a characteristic peak absorption wavelength of an antibody-coated bead bound to an analyte associated with a harmful substance). In one example for gluten detection, the photodiode system 223 can include a photodiode configured to detect absorption of 555 nm light at a detection substrate, wherein cellulose nanobeads treated with a complementary antibody for gluten have an absorption peak at 555 nm. In this example, a higher degree of absorption of 555 nm light (e.g., as indicated by a lower photodiode output) within an active region of a detection substrate 150 is associated with a higher concentration of gluten in a consumable sample, with an example of output data shown in FIG. 12.

In the second variation, the photodiode system 223 can be provided along with an illumination module 222 configured to facilitate illumination of the detection substrate 150, in order to enable detection of the analyte(s) at the detection substrate. Illumination is preferably provided at an angle (e.g., an acute angle of incidence) relative to a surface of the detection window 142, in order to minimize reflection (e.g., from the detection window 142) that could interfere with sensing by the optical sensing subsystem 220. In specific examples, the illumination module can include one or more light-emitting diodes (LEDs) and/or any other suitable light sources. The LEDs/light sources can be configured to provide light associated with an absorption peak of active particles (e.g., antibody-coated nanobeads, colloidal gold particles) at an active region of a detection substrate 150, or any suitable range of wavelengths of light. These particles can be either chemically conjugated with an antibody or more than one antibody, or can have the antibody or antibodies physically adsorbed onto them. Furthermore, in variations wherein the illumination module 222 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. The signal transduction mechanism can be based on any one or more of: absorption, fluorescence, chemiluminescence, Förster resonance energy transfer, electrical transduction, and any other suitable signal transduction mechanism. As such, illumination and or detection at an optical sensing subsystem 220 of the camera module 221 can be enabled in cooperation with one or more filters (e.g., wavelength filters, emission filters, excitation filters, etc.) configured to filter out any interfering signals.

The above variations of the optical sensor can be used in combination and/or provided by the system 100 in any suitable manner. Furthermore, in variations of a detection substrate 150 having multiple active regions, the optical sensor(s) 220 and/or illumination module(s) 222 can be provided in units, wherein the number of units is associated with a number of active regions in a detection substrate. For instance, for a detection substrate 150 having a control region and a test region, the system 100 can include two units, each having a photodiode and a light source (e.g., a 555 nm light source) configured to target each of the two active regions. In variations, however, the optical sensing subsystem 220 can be supplemented with or replaced with any other suitable sensor(s) configured to detect presence of an analyte based upon one or more of: color change, spectral emission, magnetic signals, electrical current, electrical bias, acoustic signals, and any other suitable mechanism.

3.2.D Analysis Device—Processing and Control System

The processing and control system 240 functions to receive signals from the optical sensor 240 and to generate an output indicative of presence of a harmful substance within the consumable sample, based upon signals generated from a detection substrate. The processing and control system 240 can further function to control operation of the analysis device 205, such that detection of one or more analytes associated with harmful substances in a consumable sample is, at least in part, automated. As such, the processing and control system 240 can include a processing module 242 configured to receive signals from the optical sensing subsystem 220 and a control module 244 configured to control operation of the analysis device.

The processing module 242 is preferably configured to condition signals generated at the optical sensor(s) 220, and can be directly coupled to an output of the optical sensor(s) 220. Alternatively, the processing module 242 can be configured to retrieve data generated from an output of an optical sensing subsystem 220 from a storage module or in any other suitable manner. The processing module 242 can thus be configured to perform any one or more of: denoising, filtering, smoothing, clipping, deconvolving, standardizing, detrending, resampling, and performing any other suitable signal-processing operation on output signals from the optical sensor(s) 220. In variations, wherein an output of the optical sensing subsystem 220 is image data, the processing module 242 can be configured to filter and/or condition image data for sharpness, saturation, edge-finding, intensity, and/or any other suitable image enhancement. The processing module 242 can further be configured to generate an analysis indicative of presence of the harmful substance, wherein the analysis provides information regarding an amount (e.g., concentration, volume, mass) of the harmful substance within the consumable sample. In one variation involving data from a photodiode, the analysis can enable identification of absorption peaks detected upon illumination of a detection substrate 150 (e.g., over time, taking into account kinetics of a reaction at the detection substrate), and associate an amount of absorption with an amount (e.g., concentration in parts per million) of an allergen present in the consumable sample. In one variation involving image data from a camera module, the analysis can characterize intensity (e.g., average intensity, peak intensity, relative intensity) across an active region of a detection substrate, and associate an intensity parameter (or other image parameter) with an amount (e.g., concentration in parts per million) of an allergen present in the consumable sample. The processing module 242 can be implemented in one or more processing elements (e.g., hardware processing element, cloud-based processing element), such that processing by the system 100 can be implemented in multiple locations and/or phases.

In variations, the control module 244 can be configured to control any one or more of: retaining a test container 105 within the analysis device 205 in an alignment configuration, facilitating release of the test container 105 from the analysis device 205 in the releasing configuration, depressing of a plunger 128 of the test container 105 (e.g., to transition a diaphragm 160 of the test container 105 between a first configuration and a second configuration), mixing of the homogenized sample with a process reagent upon transmission of commands to the mixing module 230, activation of a valve 138 of a second chamber 130 of the test container 105 in order to initiate delivery of a volume of a dispersion to a detection substrate 105, illumination of a detection substrate 150 upon transmission of commands to an illumination module 223, transmission of outputs of an optical sensor for conditioning an processing by the processing module 240, and any other suitable operation for automation in use of the system 100.

Modules of the processing and control system 240 can be implemented at any one or more of: on-board at the analysis device 205 that receives a test container 105, at a portion of the test container (e.g., using electronics integrated into the test container 105), and at any other suitable processing subsystem. For instance, modules of the processing and control module 240 can be implemented at a mobile device (e.g., smart phone, tablet, head-mounted computing device, wrist-mounted computing device) in communication with the analysis device 205, such that some amount of data processing and/or control of a test container 105 or analysis device 205 is implemented using the mobile device. Additionally or alternatively, modules of the processing and control system 240 can be implemented in any other hardware-based or cloud-based computing system configured to communicate with the system 100 described.

The processing and control system 240 can additionally or alternatively include a communications module (e.g., a Bluetooth low energy chip) for communication of recorded and/or stored test results to any suitable device (e.g., a user device, a remote server, etc.). However, the processing and control system 240 can be configured in any suitable manner.

Furthermore, the analysis device 205 can include any other suitable elements configured to facilitate processing of a test sample (e.g., a dispersion generated from a consumable sample that has saturated a detection substrate), and/or reporting of information derived from the test sample to a user or other entity. In one variation, the analysis device 205 can include a module configured to facilitate release of the dispersion from the port 136 of the second chamber 130 to a detection substrate 150 at an analysis chamber 140, in cooperation with a valve 138 of the second chamber 130, as described in relation to the port 136 above. The analysis device 205 can further include elements that provide an indication that the analysis device is in an operational mode (e.g., as opposed to an off mode, as opposed to a dormant mode), and/or elements that reduce noise (i.e., signal noise, acoustic noise) during processing of a test sample. The analysis device 205 can further include a housing configured to house elements of the analysis device 205 in a compact manner. The analysis device 205 or any other suitable portion of the system 100 can further include a power module configured to provide power to the system 100 (e.g., by including an energy storing, energy receiving, and/or energy distributing element) such as a battery (e.g., a rechargeable secondary battery, such as a lithium chemistry battery; a primary battery), a piezoelectric device, and/or any other suitable energy storage, generation, or conversion system. As shown in FIG. 15, the analysis device 205 and/or system 100 can additionally or alternatively include a display 250 (e.g., of the analysis device 205, of a mobile device in communication with the system 100) configured to convey information (e.g., results regarding detection of a target substance in the consumable sample) from the system 100 to a user or other entity, and/or any other suitable user interface elements (e.g., input modules, notification modules, buttons 252 for initiating and/or pausing operations of the system 100, etc.) configured to facilitate user interaction with the system 100. In a variation where the analysis device 205 defines a base 206 and two or more triangular faces 207 connected by one or more side walls, a user interface (e.g., an LED display) can be integrated with one or more of the side walls. Additionally or alternatively, the analysis device 205 can include any other suitable elements for processing of a test sample in a manner that is convenient to a user.

As a person skilled in the art will recognize from the previous detailed description and from the figures and claims, modifications and changes can be made to the embodiments of the analysis device 205 without departing from the scope of the analysis device 205.

4. Method

Figure 13:
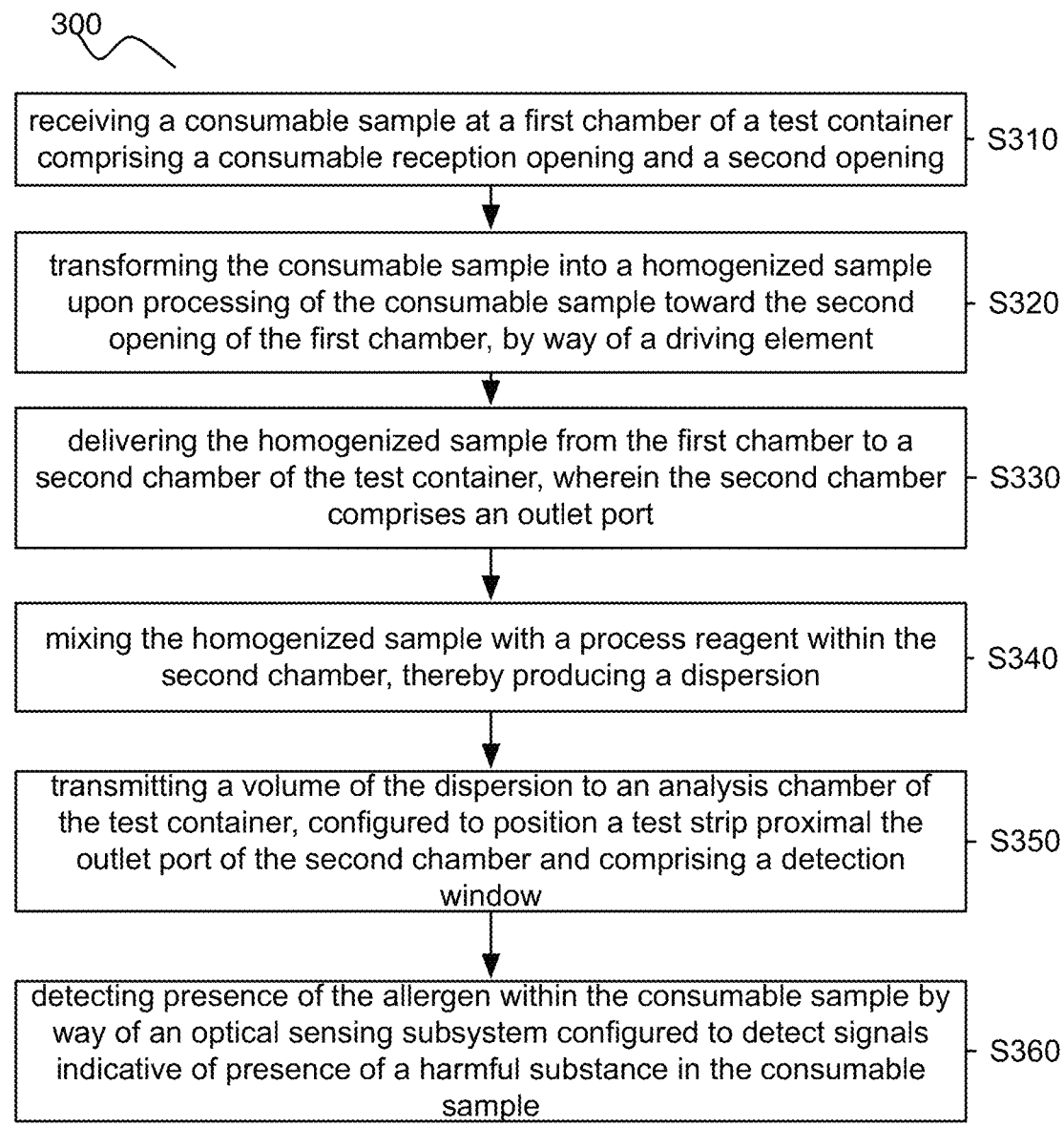
FIG. 13 depicts a flowchart schematic of an embodiment of a method for detection of harmful substances.
Figure 14:
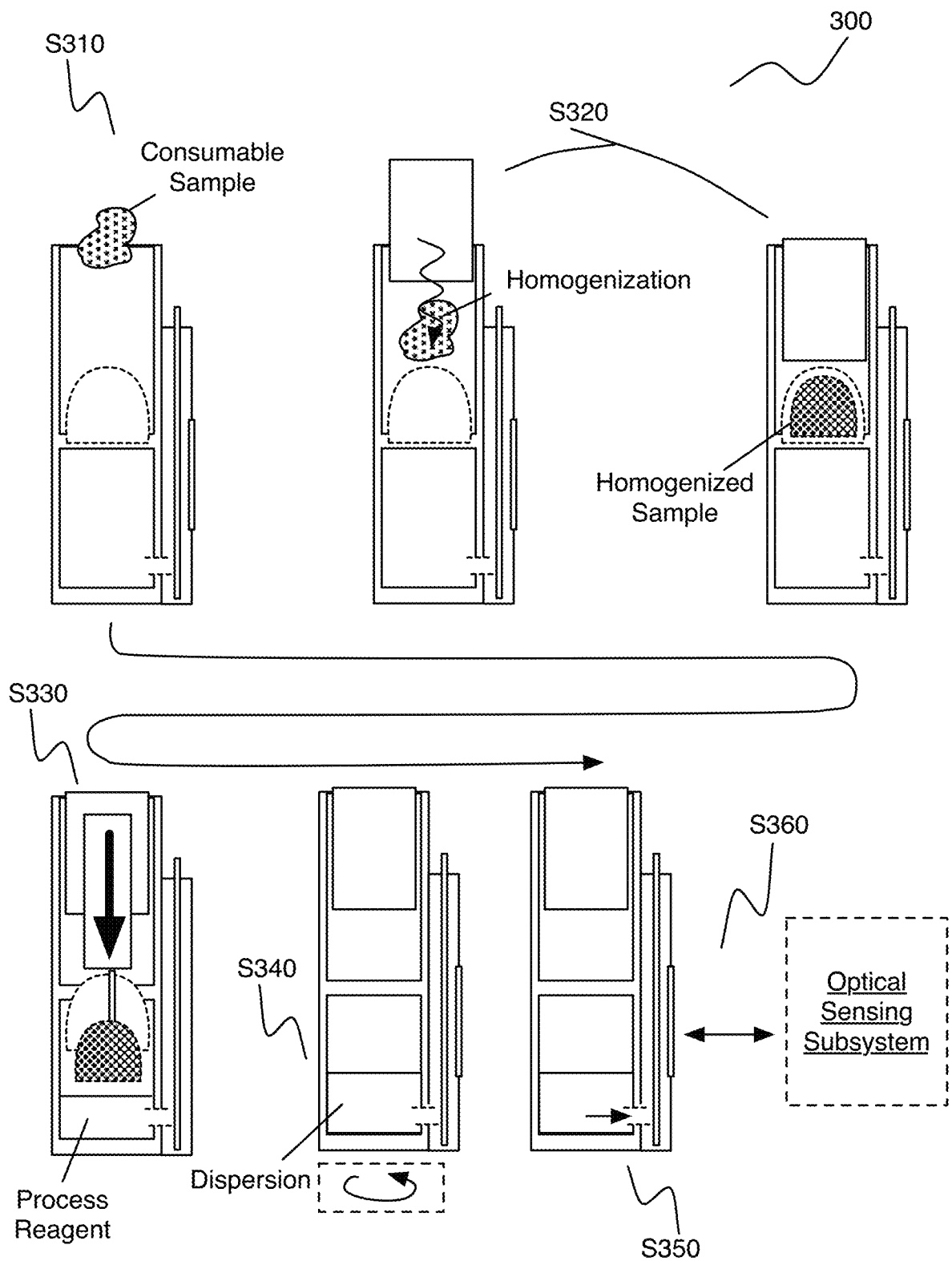
FIG. 14 depicts a schematic of an embodiment of a method for detection of harmful substances.

As shown in FIGS. 13 and 14, an embodiment of a method 300 for detecting a target substance in a consumable sample includes: receiving a consumable sample at a first chamber of a test container including a consumable reception opening, configured to receive the consumable sample, and a second opening S310; transforming the consumable sample into a homogenized sample upon processing of the consumable sample toward the second opening of the first chamber by way of a driving element S320; delivering the homogenized sample from the first chamber to a second chamber of the test container, wherein the second chamber is configured to receive the homogenized sample from the second opening of the first chamber and includes an outlet port S330; mixing the homogenized sample with a process reagent within the second chamber, thereby producing a dispersion S340; transmitting a volume of the dispersion to an analysis chamber, of the test container, configured to position a detection substrate proximal the outlet port of the second chamber and including a detection window that enables detection of presence of the allergen S350; and detecting presence of the harmful substance within the consumable sample by way of an optical sensing subsystem configured to detect signals indicative of the allergen through the detection window S360.

The method 300 functions to receive and process a sample of a consumable (e.g., food, beverage, cosmetic, etc.) in order to enable detection of one or more harmful substances within the sample. In examples, the harmful substances can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. The method 300 is preferably configured to impose minimal requirements upon a consumer using the system 100, in terms of labor-intensiveness, time-intensiveness, and cost-intensiveness. As such, the method 300 is preferably configured to automatically or semi-automatically process the sample in a manner that is intuitive to the consumer, and to quickly provide information regarding presence of the harmful substance(s) within the sample. The method 300 is preferably implemented at least in part by a portion of the system 100 described in Section 1 above; however, the method 300 can alternatively be implemented using any other suitable system.

Block S310 recites: receiving a consumable sample at a first chamber of a test container including a food reception opening, configured to receive the consumable sample, and a second opening. Block S310 functions to receive and facilitate processing (e.g., homogenization) of a consumable sample that the user intends to analyze for presence of a harmful substance. Block S310 is preferably implemented at an embodiment, variation, or example of the first chamber described in relation to the system 100 above; however, Block S310 can alternatively be implemented with any other suitable chamber configured to receive a solid and/or liquid sample. As such, Block S310 can include actively or passively receiving a consumable sample from the user. In variations of passive reception, the consumable sample can be tweezed, scooped, spooned, forked, or otherwise delivered into the first chamber in any other suitable manner. In variations of active reception, the consumable sample can be sucked or forced into the first chamber in any other suitable manner (e.g., using positive and/or negative pressure).

Block S320 recites: transforming the consumable sample into a homogenized sample upon processing of the consumable sample toward the second opening of the first chamber by way of a driving element. Block S320 functions to process the consumable sample to have particles of a desired size, and to increase homogeneity of a consumable sample received in Block S310, in order to generate reliable results regarding an amount (e.g., concentration, mass, volume) of a harmful substance within a consumable sample. Block S320 is preferably implemented using embodiments, variations, or examples of the first chamber, driving element 120, grinder 122, plunger 128, and/or diaphragm 160 of the test container 105 described in relation to the system 100 above; however, Block S320 can alternatively be implemented using any other suitable system. As such, in homogenizing the consumable sample, Block S320 preferably involves grinding the consumable sample with a set of protrusions of a driving element, using a combination of compression and rotational motions (e.g., involving threads of the first chamber and the driving element); however, Block S320 can additionally or alternatively produce the homogenized sample in any other suitable manner.

Block S330 recites: delivering the homogenized sample from the first chamber to a second chamber of the test container, wherein the second chamber is configured to receive the homogenized sample from the second opening of the first chamber and includes an outlet port. Block S330 functions to deliver the homogenized sample for further processing in a controlled manner that ensures that homogenized portions of the consumable sample continue on for further processing, while un-homogenized portions of the consumable sample are either undelivered or are retained to be homogenized. Block S330 is preferably implemented using embodiments, variations, or examples of the first chamber, driving element 120, grinder 122, plunger 128, diaphragm 160, and/or second chamber 130 of the test container 105 described in relation to the system 100 above; however, Block S330 can alternatively be performed using any other suitable system 100. As such, Block S330 can include receiving homogenized portions of a consumable sample within a cavity of a diaphragm configured between the first chamber and the second chamber, and delivering homogenized portions of the consumable sample into the second chamber by depressing a plunger configured to contact the diaphragm. Block S330 can, however, include delivering the homogenized sample from the first chamber to a second chamber of the test container in any other suitable manner.

Block S340 recites: mixing the homogenized sample with a process reagent within the second chamber, thereby producing a mixture. Block S340 functions to facilitate extraction of analytes, associated with the harmful substance, from the homogenized sample, in order to facilitate detection of the analytes in subsequent blocks of the method 300. Block S340 is preferably implemented using embodiments, variations, or examples of the second chamber 130, the mixing element 134, and/or the mixing module 230 described in relation to the system 100 described above, however, Block S240 can alternatively be implemented using any other suitable system. As such, in variations, Block S240 can include providing a volume of the process reagent (e.g., prepackaged within the second chamber), such that the homogenized sample is automatically brought into contact with the process reagent upon delivery between the first chamber and the second chamber, as described in relation to Block S330. Additionally or alternatively, Block S240 can include actively delivering the process reagent to be mixed with the homogenized sample, by way of a fluid delivery module coupled to the first chamber and/or the second chamber. In Block S240, the process reagent preferably includes an extraction solution configured to extract at least one analyte, associated with a harmful substance, from the homogenized sample, that can be detected at a detection substrate and used to indicate presence of the harmful substance. However, the process reagent can additionally or alternatively include any other suitable reagents, as described above.

While blocks of the method 300 can occur as distinct steps, in some variations, portions of at least Blocks S310, S320, S330, and/or S340 can be performed substantially simultaneously. For instance, according to a variation of the method 300, a consumable sample can combined with a process reagent (e.g., an extraction solution, a dilution buffer, etc.) prior to or during grinding, thereby producing a mixture that can be delivered from a chamber of a test container and to a detection substrate for analysis.

Block S350 recites: transmitting a volume of the dispersion to an analysis chamber, of the test container, configured to position a detection substrate proximal the port of the second chamber and including a detection window that enables detection of presence of the allergen. Block S350 functions to control delivery of the dispersion to a detection substrate, such that an adequate volume of the dispersion is provided to a detection substrate to enable analyte detection, while avoiding flooding of the detection substrate. Block S350 is preferably implemented using embodiments, variations, or examples of the second chamber, outlet port, valve, and/or analysis chamber described in relation to the system 100 above; however, Block S350 can alternatively be implemented using any other suitable system. As such, Block S350 can include opening a valve (e.g., using a control module) of an outlet port of the second chamber, to deliver a volume of the dispersion to a detection substrate within the analysis chamber. However, Block S350 can include any other suitable step for delivery of a volume of the dispersion to the detection substrate.

Block S360 recites: detecting presence of the allergen or other substances within the consumable sample by way of an optical sensor configured to detect signals indicative of the allergen through the detection window. Block S360 functions to detect and process signals generated from a detection substrate treated with the dispersion, in order to generate an analysis that provides information regarding presence of one or more harmful substances within a consumable sample. Block S360 is preferably implemented using embodiments, variations, or examples of the analysis chamber, detection substrate, detection window, optical sensor, and/or processing and control system described in relation to the system 100 above; however, Block S360 can alternatively be performed using any other suitable system. As such Block S360 can include any one or more of: denoising, filtering, smoothing, clipping, deconvolving, standardizing, detrending, resampling, and performing any other suitable signal-processing operation on output signals from an optical sensor in communication with a detection substrate saturated with the dispersion. In variations of Block S360 involving image data, Block S360 can include filtering and/or conditioning image data for sharpness, saturation, edge-finding, intensity, and/or any other suitable image enhancement.

In generating an analysis in Block S360, the analysis preferably provides information regarding an amount (e.g., concentration, volume, mass) of the harmful substance within the consumable sample. In one variation involving data from a photodiode, generating the analysis in Block S360 can include identifying absorption peaks detected upon illumination of a detection substrate 150 (e.g., over time, taking into account kinetics of a reaction at the detection substrate), and associating an amount of absorption with an amount (e.g., concentration in parts per million) of an allergen present in the consumable sample. In one variation involving image data from a camera module, generating the analysis in Block S360 can include characterizing intensity (e.g., average intensity, peak intensity, relative intensity) across an active region of a detection substrate, and associating an intensity parameter (or other image parameter) with an amount (e.g., concentration in parts per million) of an allergen present in the consumable sample. Block S360 can, however, include processing signals derived from a detection substrate saturated with a volume of the dispersion, and/or generating an analysis in any other suitable manner.

The method 300 can additionally or alternatively include any other suitable blocks or steps configured to facilitate reception and/or processing of a consumable sample, in order to facilitate detection of the presence of one or more harmful substances within the consumable sample.

In relation to the system 100, the test container 105, the analysis device 205, and/or the aligned system of a test container 105 coupled to the analysis device can have any suitable dimensions (e.g., width, length, height, surface area, volume, aspect ratio, curvature, flat, etc.). Additionally or alternatively, components of the system 100 can be defined by any suitable three-dimensional shapes including: a prism (e.g., triangular prism, square prism, polygonal prism, etc.), cube, cylinder, sphere, plate and/or any suitable three-dimensional shape. The shape of a surface area of a component of the system 100 can include: a rectangle, square, circle, triangle, polygon, and/or other suitable shape.

Embodiments of the system 100 and/or method 300 and variations thereof can be embodied and/or implemented at least in part by a machine configured to receive a computer-readable medium storing computer-readable instructions. The instructions are preferably executed by computer-executable components preferably integrated with the system 100 and one or more portions of the processor 273 and/or the controller 272. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A test container for detecting a harmful substance, the test container comprising:
   a first chamber configured to receive a sample;
   a second chamber positioned below the first chamber and configured to be in fluid communication with the first chamber, the first chamber vertically aligned with the second chamber, the first chamber or the second chamber including a reagent that produces a dispersion when combined with the sample;
   an analysis chamber in fluid communication with the second chamber; and
   a detection substrate positioned within the analysis chamber, the detection substrate being positioned entirely outside the second chamber, the detection substrate including a test strip;
   wherein the sample is configured to be placed within the first chamber, combine with the reagent in the first chamber or the second chamber, and flow from the second chamber into the analysis chamber to be detected by the detection substrate to detect the harmful substance within the sample;
   wherein the detection substrate includes an active region having an antibody that is complementary with the harmful substance;
   wherein the detection substrate includes a control region to provide a control readout;
   wherein the detection substrate is configured to soak up a portion of the dispersion, the portion of the dispersion being positioned within the analysis chamber prior to being soaked up by the detection substrate, and
   wherein the portion of the sample moves upwardly along the detection substrate via a capillary flow.

2. The test container of claim 1, wherein the harmful substance is a food allergen.

3. The test container of claim 1, further comprising a detection window, and
   wherein the detection window facilitates observation of the active region of the detection substrate.

4. The test container of claim 1, wherein the first chamber is in selective fluid communication with the second chamber.

5. The test container of claim 4, wherein the first chamber includes a first opening configured to receive the sample for placement into the first chamber, and a second opening opposite the first opening, and wherein the test container further comprises a diaphragm positioned between the first chamber and the second chamber, the diaphragm extending across the second opening.

6. The test container of claim 5, wherein the diaphragm is configured to move between a first configuration and a second configuration,
wherein in the first configuration the diaphragm retains the sample within the first chamber, and
wherein in the second configuration the diaphragm facilitates delivery of the sample from the first chamber to the second chamber.

7. The test container of claim 6, wherein the diaphragm is configured to break thereby transitioning the diaphragm from the first configuration to the second configuration to release the sample from the first chamber into the second chamber.

8. The test container of claim 7, further comprising:
a body; and
a cap that is configured to engage with the body of the test container to seal the test container, and
wherein when the cap seals the test container, the diaphragm is configured to break to release the sample from the first chamber into the second chamber.

9. A test container for detecting a harmful substance, the test container comprising:
a first chamber configured to receive a sample;
a second chamber positioned below the first chamber and configured to be in fluid communication with the first chamber, the first chamber vertically aligned with the second chamber, the first chamber or the second chamber including a reagent that produces a dispersion when combined with the sample;
an analysis chamber in fluid communication with the second chamber; and
a detection substrate that includes a test strip, the detection substrate including an active region having an antibody that is complementary with the harmful substance that is a food allergen, the detection substrate positioned within the analysis chamber and entirely outside the second chamber;
wherein the sample is configured to be placed within the first chamber, combine with the reagent in the first chamber or the second chamber, and flow from the second chamber into the analysis chamber to be detected by the detection substrate to detect the harmful substance within the sample;
wherein the detection substrate is configured to soak up a portion of the dispersion from within the analysis chamber, and
wherein the portion of the sample moves upwardly along the detection substrate via a capillary flow.

10. The test container of claim 9, further comprising a port positioned between the analysis chamber and the second chamber, the port facilitating fluid communication between the analysis chamber and the second chamber.

11. The test container of claim 9, further comprising a cap that is configured to threadingly engage a body of the test container to seal the test container.

12. The test container of claim 11, wherein the cap includes a shaft and a head,
wherein the shaft is configured to be inserted into the first chamber, and
wherein the head has a larger width than a width of the first chamber.

13. The test container of claim 9, further comprising a detection window that facilitates observation of the active region of the detection substrate.

14. The test container of claim 9, wherein the first chamber includes a reagent;
wherein the sample that includes the harmful substance is configured be placed within the first chamber, combined with the reagent in the first chamber, directed into the second chamber, and directed into the analysis chamber so that the harmful substance in the sample is detected by the detection substrate.

15. The test container of claim 9, further comprising a diaphragm positioned between the first chamber and the second chamber; and
wherein the diaphragm is configured to break thereby transitioning the diaphragm from a first configuration that retains the sample within the first chamber to a second configuration to release the sample from the first chamber into the second chamber.

16. The test container of claim 15, further comprising:
a body; and
a cap that is configured to engage with the body of the test container to seal the test container; and
wherein when the cap seals the test container, the diaphragm is configured to break to release the sample from the first chamber into the second chamber.

17. A test container for detecting a harmful substance, the test container comprising:
a first chamber configured to receive a sample, the first chamber including a first opening configured to receive the sample for placement into the first chamber, and a second opening opposite the first opening;
a second chamber positioned below the first chamber and configured to be in fluid communication with the first chamber, the first chamber vertically aligned with the second chamber, the first chamber or the second chamber including a reagent that produces a dispersion when combined with the sample;
a diaphragm positioned between the first chamber and the second chamber, the diaphragm extending across the second opening, the first chamber being in selective fluid communication with the second chamber;
an analysis chamber in fluid communication with the second chamber; and
a detection substrate positioned within the analysis chamber, the detection substrate being positioned entirely outside the second chamber, the detection substrate including a test strip; and
wherein the sample is configured to be placed within the first chamber, combine with the reagent in the first chamber or the second chamber, and flow from the second chamber into the analysis chamber to be detected by the detection substrate to detect the harmful substance within the sample.

18. The test container of claim 17, wherein the diaphragm is configured to break thereby transitioning the diaphragm from a first configuration that retains the sample within the first chamber to a second configuration to release the sample from the first chamber into the second chamber.

19. The test container of claim 18, further comprising:
a body; and
a cap that is configured to engage with the body of the test container to seal the test container; and
wherein when the cap seals the test container, the diaphragm is configured to break to release the sample from the first chamber into the second chamber breaks; and wherein the harmful substance is a food allergen.

20. The test container of claim 1, wherein the harmful substance is gluten.

21. The test container of claim 9, wherein the harmful substance is gluten.

22. The test container of claim 17, wherein the detection substrate is configured to detect the harmful substance that is gluten.

23. The test container of claim 9, further comprising a grinder that is configured to grind the sample within the first chamber.

24. The test container of claim 9, further comprising a magnet positioned within the second chamber that is configured to rotate within the second chamber.

25. The test container of claim 9, wherein the test container is configured to be received within a receiving port of an analysis device.

\* \* \* \* \*

UNITED STATES PATENT AND TRADEMARK OFFICE
CERTIFICATE OF CORRECTION

PATENT NO. : 12,031,979 B2
APPLICATION NO. : 16/704184
DATED : July 9, 2024
INVENTOR(S) : Scott Sundvor et al.

It is certified that error appears in the above-identified patent and that said Letters Patent is hereby corrected as shown below:

In the Specification

Column 15, Line 20, "160 and/or" should be --160) and/or--.

Column 28, Line 24, "150 are" should be --150) are--.

Column 41, Line 65, "S240" should be --S340--.

Column 41, Line 66, "S240" should be --S340--.

Column 42, Line 5, "S240" should be --S340--.

Column 42, Line 9, "S240" should be --S340--.

Signed and Sealed this
Nineteenth Day of November, 2024

Katherine Kelly Vidal
*Director of the United States Patent and Trademark Office*